(12) United States Patent
Kanhonou et al.

(10) Patent No.: US 7,427,697 B2
(45) Date of Patent: Sep. 23, 2008

(54) SUGAR BEET GENES INVOLVED IN STRESS TOLERANCE

(75) Inventors: Arthur Rodolphe Kanhonou, Valencia (ES); Ramon Serrano Salom, Valencia (ES); Roc Ros Palau, Valencia (ES)

(73) Assignee: CropDesign, Gent (BG)

( * ) Notice: Subject to any disclaimer, the term of this patent is extended or adjusted under 35 U.S.C. 154(b) by 0 days.

(21) Appl. No.: 11/724,658

(22) Filed: Mar. 15, 2007

(65) Prior Publication Data

US 2008/0057582 A1 Mar. 6, 2008

Related U.S. Application Data

(62) Division of application No. 10/451,554, filed on Jan. 26, 2004, now Pat. No. 7,227,053.

(51) Int. Cl.
| | |
|---|---|
| C12N 15/82 | (2006.01) |
| C12N 15/29 | (2006.01) |
| A01H 5/00 | (2006.01) |
| C07H 21/00 | (2006.01) |

(52) U.S. Cl. .................. 800/289; 435/468; 435/320.1; 536/23.1; 536/23.6; 800/278

(58) Field of Classification Search ........................ None
See application file for complete search history.

(56) References Cited

U.S. PATENT DOCUMENTS

| 5,891,859 A | 4/1999 | Thomashow et al. |
|---|---|---|
| 2004/0025202 A1 | 2/2004 | Laurie et al. |

OTHER PUBLICATIONS

Lin et al., NCBI, GenBank, Sequence Accession No. AC006951, Published Apr. 17, 1999.*
Keskin et al. (2004) *Protein Science*, 13:1043-1055.
Thorton et al. (2000) *Natural Structural Biology, Strutural Genomics Supplement.*
Guo et al. (2004) *PNAS*, 101, 9205-9210.
Zhu et al. (2001) *Current Opinion in Plant Biology*, 4:401-406.
Jeong et al. (2000) "Isolation and Characterization of the Gene Encoding Glyceraldehyde-3-Phosphate Dehydrogenase" *Biochem. Biophys. Res. Commun.*, 278:192-196.
Kleinow et al. (2000) "Functional identification of an *Arabidopsis* Snf4 ortholog by screening for heterologous multicopy suppressors of snf4 deficiency in yeast", *The Plant Journal* 23:115-122.
Peracchia et al. (1998) "Casein kinase II alpha subunit; CK2 gene", *EMBL* Accession No. Y11526.
Piao et al. (1999) "An Arabidopsis GSK3/shaggy-like gene that complements yeast salt stress-sensitive mutants is induced by NaCl and abscisic acid" *Plant Physiol.*, 119:1527-1534.
Winicov et al. (1998) "New Molecular Approaches to Improving Salt Tolerance in Crop Plants", *Annals of Botany*, 82:703-710.
Peracchia et al. (1999) "Characterization, subcellular localization and nuclear targeting of casein kinase 2 from *Zea mays*" *Plant Mol. Biol.* 40, 199-211.

* cited by examiner

*Primary Examiner*—Phuong T Bui
*Assistant Examiner*—Vinod Kumar
(74) *Attorney, Agent, or Firm*—Ann R. Pokalsky; Dilworth & Barrese, LLP

(57) ABSTRACT

The present invention relates to isolated genes originating from *Beta vulgaris*, sugar beet, that are involved in responses to stress situations. The genes were isolated from a sugar beet cDNA library screened in a functional selection procedure with transformed yeast cells that were able to grow in selection medium with high salt concentrations. Subsequently these genes were sequenced and further characterized. One of the genes is a sugar beet casein kinase α subunit, one is a sugar beet dihydroorotase, one is a sugar beet translation initiation factor 1A and two others are of a unknown protein type. All of these isolated plant genes were functional as stress tolerance enhancers in yeast cells and are therefore useful to confer stress tolerance to an organism when transfected herein. More particularly, these genes can be used to render crops resistant to stress situations like osmotic stress caused by salt, drought, cold or frost.

31 Claims, 12 Drawing Sheets

FIGURE 1

Figure 2:
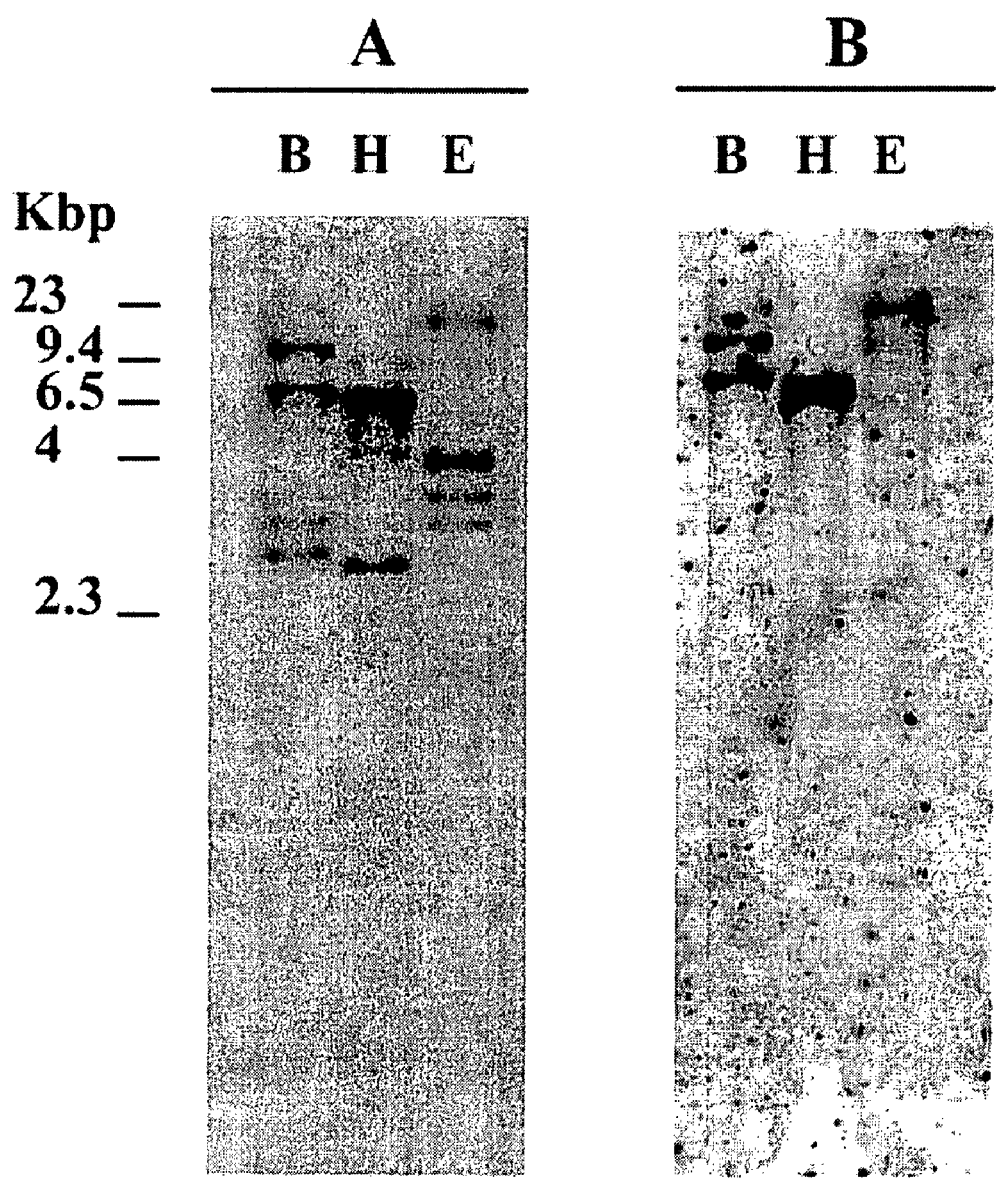

Figure 6:

SEQ ID NO 1 : DNA sequence of the red beet gene clone 154 BvCK2 (casein kinase α catalytic subunit)

```
GAATTCGGCACGAGGAAATTTGAGATTGTCGGGTTCACTCCTCTTCACACTACTAACTTTTT
TCCATCTTCTCTCTCACTCGTCTTACTGTGCGCACTCCTTGCTCTCCGTGCACCGGTGGCGC
ATCCTCCTATCCTGCGCCCATCAACCCTAAATTTCGCCGCCGCTAATTTCGAGATCTCCGCC
GACGCAAATTCTCCGATGTCGAAGTCGCGAGTTTACGCCGACGTTAATGTTCTCCGACCTCG
AGAGTACTGGGATTACGAAGCTCTCACTGTTCAATGGGGTGATCAAGATGACTATGAAGTCG
TGCGGAAGATTGGAAGGGGGAAATACAGTGAAGTTTTTGAAGGATTAAACGTCAATAGTAAT
GAACGATGCGTTATCAAGATCCTGAAACCTGTGAAGAAGAAAAAGATCAAAAGAGAGATAAA
AATCCTTCAGAACCTATGTGGGGGACCAAACGTCATAAAGCTGCTTGATATCGTCAGGGATC
AGCACTCCAAAACACCAAGCTTAGTTtTTGAGTTTGTCAACAGTACAGATTTCAAAGTTCTG
TATCCAACGTTATCTGATTATGACATACGTTATTACATCTATGAGCTTCTGAAGGCCTTAGA
TTTCTGCCATTCACAAGGGATAATGCACCGAGATGTCAAGCCTCATAATGTAATGATAGACC
ATGAATTGAGGAAACTCCGGTTAATAGATTGGGGTCTGGCAGAGTTCTACCATCCAGGGAAG
GAATACAATGTTCGTGTGGCTTCGAGATACTTTAAGGGGCCGGAACTTCTTGTTGATTTACA
AGACTATGACTATTCCTTGGACATGTGGAGCCTTGGTTGCATGTTTGCTGGGATGATTTTCC
GGAAAGAACCATTCTTCTATGGTCATGACAACCATGATCAGCTTGTTAAAATTGCTAAGGTA
CTTGGAACAGATGAACTGAATGCTTATTTGAACAAGTATCATTTGGAGCTTGATCCTCAACT
TGATGCTCTTGTTGGAAGGCACAGCAGGAAGCCATGGTCAAGATTTGTTAATCCGGATAATC
AGCATTTAGTTTCCCCTGAGGCTATTGACTTTCTTGATAAGCTTCTTCGCTATGACCACCAG
GATAGGCTTACTGCAAAAGAAGCAATGGCACATCCTTATTTCTCTCAAGTTAGAGCTGCAGA
GAGTAGCAGAATGCGGACACAATAGCTCGTCACTCTAATACATACTTGAGAATGATGATTTC
CATTGTAGAGTGTTTCATGTTAAGTCATTGACTGTGTTCCCGTCTTAAACATTGCAGCTACT
TGCAGCGTCAGGTAGACAGCTTTGATTGCGCGGGGAAATTTTATGTAAAATGCATGATTACT
AGTCTTTCTAAAACTGCAAATCTGCAATGCCACAAACTATTGTACTGCTATTTTAATTGTTG
AAGCCCTCTGTACATCTCCAACATTGGTTGTCACTTAATATAGTTTGCTAATAGCATCTGTA
AAAAAAAAAAAAAAAAAAAAAAAAAAAAAAAAAAAAA
```

SEQ ID NO 2 : DNA sequence of the red beet gene clone 35 BvDHO (dihydroorotase)

```
AATTCGGCACGAGCACAGCTCCACTCCCTCTTTCTCTCAAGAAGACGAACACACACCAATTC
AGATCTGAAGTTTCGTATTTTCTCTCTCCTCTTCCTCGACATCTTCCTCGTGCTCGAATTGC
AAGCGTTCCAGGCATCAAATTTGCCTATTCCCGGGTTTGAAACACATAACGGACTAAATATC
AAAGCAGTAAAGATGGAACTGACTCTTACACGCCCTGATGACTGGCATCTACATCTCCGCGA
TGGAGATCTTCTTGCTGCTGTTGCTCCTCACAGTGCAAGACATTTTGGAAGGGCAATCGTTA
TGCCGAATCTAAGGCCTCCTGTTACTACTACAGGTGCTGCTATTGCTTACCGAAAGTCTATT
ATGGAAGTATTGCCTGATGATAGCGACTTCAATCCTCTCATGACACTTTATTTGACTGATAC
GACCAGCCCTAATGAGATCAAGCTTGCCAGAAAAGTGAGGTGGTATATGCTGTCAAATTAT
ACCCTGCTGGCGCAACAACTAATTCTCAGGACGGTGTCACTGATCTTTTAGGAAAGTGTCTG
CCTGTGCTTGAAGAGATGGCTGAGCAAGATATGCCTCTTCTGGTCCATGGAGAAGTTACAGA
TCCTGATGTAGATATATTTGATCGTGAAAAGGTTTTTATTGAGTCAGTTTTAAGACCTTTAA
TTCAGAAATTACCACAGCTAAAGGTTGTGATGGAACACATCACTACTGCTGATGCTGTCAAG
TTTATTGAGTCCTGTAATGGAGGAAATGTAGCAGCCACTGTGACGCCGCAGCACCTTGTTCT
GAATAGAAACTCTCTCTTCCAAGGAGGGTTGCAACCGCATAACTATTGTCTTCCAGTGCTCA
AAAGAGAAATCCATAGACAGGCACTTGTTTCAGCGGTAACCAGCGGGAGCAAGCAATATTTT
CTTGGGACTGATAGTGCTCCTCATGAAAGGCGGAGGAAAGAATGTTCGTGTGGATGTGCTGG
```

```
AATCTATAATTCCCCTGTTGCTCTATCACTATATGCCAAAGTATTTGAAGAGGCTGGTGCCC
TTGACAAGTTAGAGGCATTTACAAGCTTTAATGGACCCGATTTCTATGGTCTTCCAAGGAAT
ACGTCGAAGATCAAGTTGAAAAAAGAACCATGGAAAGTCCTAGAGCGTATACCTTTCCCATC
CGGAGAAATAATCCCTATGTTTGCTGGACAAATGCTTGACTGGAAGCCATCTTTCTGAGATC
ATCTCTCATCCATCTTTACCATCTGTACTTTCCCTTTCTTTCAATGCATTTGTGTCTCATTG
ATGAGAAATGTGTACTGCTTGAACATCAATTTTGTGGGCACTCAGTTTGTAAGACCTCTTAC
CTTTTTTAGAAAGAAACAAGGACCAACAAGTGCTTGGATCAGGTGGTAGTAAGAGGTTTCGG
CTCAATCAAAGGATTCAGATTCGAGCTTCAAGCACTTGTTCGGAGAGCTCCCCCCAATCGAG
CCTTCCGCGCCCGAATCTACGGTCGTTCGAACTCTGGTAGGCTCTAAATTACTGGGTGTTTT
TCTTTATCTTCTCCCCCTTTAAATGAAAAAAGGGGGCACAGATTATAAGTTCCAATTTAAT
TTCTACAAGACAAATTTATAATAATTCTAATAAAGTTCTATACCAGCTTAATCTTACCTTTA
TTTTAAAAAAAaAAAAAaAAAaAaAaaAAAaaaAAAaaAaaAAAAAAAAAaAaaAaAAAaaA
AAAAaAa
```

SEQ ID NO 3 : DNA sequence of the red beet gene clone 76 BveIF-1A (translation initiation Factor 1A)

```
CTAGCAAACAACAACAAACTCAAAAACCAGCCTTTTTTTCACAAAATCAGAACCGTCTGATC
TAGGGTTTTCTGGTAGAGAGAAAAGATGCCGAAGAACAAAGGAAAGGGAGGAAAGAACAGGA
AGAGAGGAAAGAATGAAGCTGATGATGAGAAAAGAGAACTTGTTTTCAAAGAAGATGGACAA
GAGTACGCGCAAGTTGTTCGTATGCTCGGTAATGGCCGTTGTGAAGCTACTTGCATCGATTA
TGTTAAGCGTCTTTGTCATATTCGTGGTAAGATGCACAAAAAAGTCTGGATCGCTGCTGGTG
ATATTATTCTCGTCGGTCTTCGCGATTATCAGGATGACAAGGCTGATGTGATCCTAAAGTAT
ATGCCAGATGAAGCCAGGTTGCTCAAAGCTTACGGCGAGTTGCCAGACAACATCAGACTTAA
TGAAGGTGTTGCTAATCTCGATGAGGAAGACGATGGTGGTGCTGATGACTACATCGAGTTCG
AAGACGAAGACATTGATAAGATATAAGCAATTTAAGTTTGTTTACAAATGCACCTTTACTGC
GACTGTTGAACCTTATATGTCAATTGTATGTTTCTTGGGTTTGATCAATATTTGATGTAAAA
AAAAAAAAAAAAAA
```

SEQ ID NO 4 : DNA sequence of the red beet gene clone 120 Bv120 (putative protein)

```
TGTCAGTCACAATCATCAGACTATATCAATGGTTCGTAAGCGATTTCAAGACGTGCAAACAG
GTATTCAATGGGCTAAAGTGTTGAGAAAAGTGGGATTAGGCAAGGAAGACAGGTACTTTTGG
AAGCAAGTGGGTAAGGCATTGCTATGCACCTATGCAGTGTTTGGTGCAGCATGGGTTTACAA
TGAAACATCACCACTTGGGTGGTGGACATTGAAGCCTCGTCCTAAGGAGGAGAAAGAACTAG
CTCATCTTTACGAACGGCGAGAGTTTCCGTATCCAGGTGACAAAGAAGCAATGGAAGAGTTT
GTAACCAAAGGTGGGATGATTGGTACTACCATTGGCCCGAAAGGAACAGTTGAAACTGATAA
GGATTCATTTAACTATCAGAAAGCATTGCAGGATAAGAAGTTTGAGCAGGAGGCTCATAAGT
TGTGGTTTAGGATGAGGAATGAAGTGGTTGCGGAGCTTCAAGAAAAGGGTTTCGATGTCGAG
TGATACGATTAGGAATGGCAATGACAATAACATCAAGCCTCTAGGTGAAGTATTTGTTTTGA
ACTGGTTTGTGTTAGCTTATTAGCTTTGTGGAAATAATGCCTTGGTTTGTGGTGCTTTAAGT
TTAAGGATTGAACATATATATTGTTTGGGACTTGAGAGTTCCAAGAAAAGGGTTTTGATGTC
AGTGAAACAATTGAGGAATGGCAATGACAATTACATCAAGCCTCTATAGGTGAAGTATGGTC
TGAACTAATTCTGTTAGCCTTAAGTTGTGTGCCTTAAAGTTTAAGGATTGAACATATCTATA
ATTGGGACTTGAGAATGGGACAATAAGATACAATTGGGG
```

SEQ ID NO 5 : DNA sequence of the red beet gene clone 20Li Bv20Li (unknown protein)

```
ATGATGGGTGAAGGTAACAGGGACAAGAGTAAGAAGAAGAAGAAGAAGAGAGGTGGTGCTAA
AAGAAGGATGACTGTTGAACAAACTTCAGCTTTGAAATCTGTAAATGAATGGGTTTATTTGG
CTCAACATGCTGATGAACAAGAGAAGATCAAAGAGGATGATTTTCTACCTGAAATTATGCGC
ATTGCTAGAGTTTCTGAGAATATTGTGTTTGAATTGCATTCTCATACTATTTGCAGTGATGG
GTTTTTATCCCCTTCTGCTCTTGTTGAGAAAGCTCATCAAAATGGGGTGAAAGTTCTTGCTT
TGACTGATCATGACACAATGtCTGGTATCCCCGAGGCCCTGCAAGCGGCCGGTAGATTTGGT
ATCAAGATTATTCCAGGTGTTGAGATCAGTTCAGTTTTCTCTACTACAAGAGATGAATCTGA
AGCAGAAGAACCAGTTCACATTCTTGCATATTATAGCAGCTGTGGACCTGCAAGATTTGAAG
AGTTAGATCAATTTTTGGCCAACATAAGGGACGGACGTTACCTTCGTGCCAAAAATATGCTC
GCAAAACTTGCGAAACTCAAAAAGCCCGTCAAGTGGGAACGTGTCATAAAGATTGCAGGCAA
TGGAGTTGCTCCTGGGAGACTGCATGTAGCTCGTGCTTTGTTGGAAGCTGGCCATGTTGAAG
ATCTTAAACAAGCATTCGATCGGTATCTTCATGATGGGGCCCTGCTTATTCCAAGGGAAGT
GAGCCTTCTGCGGAAGAAGCTGTGCAAATGGTGTGTAAAACTGGGGGAATAGCTGTCTTGGC
ACATCCATGGGCATTAAAAAATCCTTCCCCAGTAGTCAACAGATTGAAAGGAGGCAGGTCTT
CATGGAATTGA
```

SEQ ID NO 6 : amino acid sequence of the red beet gene clone 154 BvCK2 (casein kinase α catalytic subunit)

```
MSKSRVYADV  NVLRPREYWD  YEALTVQWGD  QDDYEVVRKI  GRGKYSEVFE
GLNVNSNERC  VIKILKPVKK  KKIKREIKIL  QNLCGGPNVI  KLLDIVRDQH
SKTPSLVFEF  VNSTDFKVLY  PTLSDYDIRY  YIYELLKALD  FCHSQGIMHR
DVKPHNVMID  HELRKLRLID  WGLAEFYHPG  KEYNVRVASR  YFKGPELLVD
LQDYDYSLDM  WSLGCMFAGM  IFRKEPFFYG  HDNHDQLVKI  AKVLGTDELN
AYLNKYHLEL  DPQLDALVGR  HSRKPWSRFV  NPDNQHLVSP  EAIDFLDKLL
RYDHQDRLTA  KEAMAHPYFS  QVRAAESSRM  RTQ*
```

SEQ ID NO 7 : amino acid sequence of the red beet gene clone 35 BvDHO(dihydroorotase)

```
MELTLTRPDD  WHLHLRDGDL  LAAVAPHSAR  HFGRAIVMPN  LRPPVTTTGA
AIAYRKSIME  VLPDDSDFNP  LMTLYLTDTT  SPNEIKLARK  SEVVYAVKLY
PAGATTNSQD  GVTDLLGKCL  PVLEEMAEQD  MPLLVHGEVT  DPDVDIFDRE
KVFIESVLRP  LIQKLPQLKV  VMEHITTADA  VKFIESCNGG  NVAATVTPQH
LVLNRNSLFQ  GGLQPHNYCL  PVLKREIHRQ  ALVSAVTSGS  KQYFLGTDSA
PHERRRKECS  CGCAGIYNSP  VALSLYAKVF  EEAGALDKLE  AFTSFNGPDF
YGLPRNTSKI  KLKKEPWKVL  ERIPFPSGEI  IPMFAGQMLD  WKPSF*
```

SEQ ID NO 8 : amino acid sequence of the red beet gene clone 76 BveIF-1A (translation initiation Factor 1A)

```
MPKNKGKGGK  NRKRGKNEAD  DEKRELVFKE  DGQEYAQVVR  MLGNGRCEAT
CIDYVKRLCH  IRGKMHKKVW  IAAGDIILVG  LRDYQDDKAD  VILKYMPDEA
RLLKAYGELP  DNIRLNEGVA  NLDEEDDGGA  DDYIEFEDED  IDKI*
```

SEQ ID NO 9 : amino acid sequence of the red beet gene clone 120 Bv120 (putative protein)

```
MVRKRFQDVQ  TGIQWAKVLR  KVGLGKEDRY  FWKQVGKALL  CTYAVFGAAW
VYNETSPLGW  WTLKPRPKEE  KELAHLYERR  EFPYPGDKEA  MEEFVTKGGM
IGTTIGPKGT  VETDKDSFNY  QKALQDKKFE  QEAHKLWFRM  RNEVVAELQE
KGFDVE*
```

SEQ ID NO 10 : amino acid sequence of the red beet gene clone 20Li Bv20Li (unknown protein)

```
MMGEGNRDKS  KKKKKKRGGA  KRRMTVEQTS  ALKSVNEWVY  LAQHADEQEK
IKEDDFLPEI  MRIARVSENI  VFELHSHTIC  SDGFLSPSAL  VEKAHQNGVK
VLALTDHDTM  SGIPEALQAA  GRFGIKIIPG  VEISSVFSTT  RDESEAEEPV
HILAYYSSCG  PARFEELDQF  LANIRDGRYL  RAKNMLAKLA  KLKKPVKWER
VIKIAGNGVA  PGRLHVARAL  LEAGHVEDLK  QAFDRYLHDG  GPAYSKGSEP
SAEEAVQMVC  KTGGIAVLAH  PWALKNPSPV  VNRLKGGRSS  WN*
```

SUGAR BEET GENES INVOLVED IN STRESS TOLERANCE

CROSS REFERENCE TO RELATED APPLICATIONS

The present application is a divisional of U.S. application Ser. No. 10/451,554, filed Jan. 26, 2004, now U.S. Pat. No. 7,227,053, which claims priority of U.S. Provisional Application No. 60/271,656, filed Feb. 26, 2001.

FIELD OF INVENTION

The present invention relates to the field of plant molecular biology, more particularly to the use of sugar beet genes and proteins, able to confer a phenotype in eukaryotic cells or organisms of tolerance to stress situations for example mineral salt toxicity caused by ions such as Na+ or Li+.

BACKGROUND

Soil salinity is one of the most significant abiotic stresses for plant agriculture and therefore it would be useful to identify and isolate stress tolerance genes for the practical goal of genetically improving the salt tolerance of crop plants.

Two other major abiotic stresses, drought and cold, are intimately linked with salt stress. Many genes that are regulated by salt stress are also responsive to drought or cold stress (Zhu, 1997), therefore these genes are particularly interesting for genetically improving of stress tolerance.

The molecular mechanisms by which plants respond to salt stress are starting to be elucidated (Hasegawa et al. 2000a). The sodium transporters at the vacuole and plasma membrane, identified as the products of the *Arabidopsis* NHX1 (Gaxiola et al. 1992, Apse et al. 1999) and SOS1 (Shi et al. 2000) genes respectively, have been described as important determinants of salt tolerance.

For the goal of genetically improving stress tolerance in plants it is important to use stress tolerance genes that when introduced can immediately confer stress tolerance. The action of these genes cannot be dependent on other pathway-related events or other components that are necessary for the molecular mechanism of stress tolerance. One can identify important stress factors in the stressed organism, but the question remains whether these genes will also contribute in enhancing stress tolerance in a heterologous host when isolated and transfected herein.

Sugar Beet (Genes) and Stress

It is known that *Beta vulgaris* L. (Chenopodaceae, sugar beet), is rather a stress resistant plant when compared to other plants e.g. *Arabidopsis thaliana*. Sugar beets are relatively spoken rather stress resistant to salt- and drought. The genes that are responsible for the ability of sugar beet to grow in more difficult conditions are started to be elucidated. A first indication that a gene under investigation might be involved in the induction of resistance, is the increase of its expression under stress conditions. As an example, Matthias et al. (1996) showed that salt stress induces the increased expression of V-type H+ATPase in mature sugar beet leaves. Also betaine, an osmoprotectant, is accumulated by many beet plants in response to salinity and drought. Furthermore in sugar beet, the expression of Choline monooxygenase, which catalyzes the committing step in the synthesis of glycine betaine of sugar beet, is also induced by osmotic stress in Chenopodaceae. The mRNA levels in leaves increased 3- to 7-fold at 400 mM salt and returned to uninduced levels (Russel, 1998).

As mentioned above there are several alternative pathways to respond to stress situations and therefore many different genes are probably involved in stress responses.

SUMMARY OF THE INVENTION

In the present invention five novel genes were isolated from *Beta vulgaris* and were transformed to yeast cells. These genes all induced stress tolerance in the yeast cells, and encode for a casein kinase α subunit, referred to as BvCK2A, a dihydroorotase, referred to as BvDHO, a translation initiation factor 1A, referred to as BveIF-1A, and for two other unknown proteins, further referred to as Bv120 and By20Li.

Unexpectedly, the inventors demonstrated that these sugar beet genes when transformed in yeast could render this heterologous organism tolerant to stress, Na+ stress in particular. The surprisingly strong phenotype of some of these yeast clones and the fact that these genes in an isolated position and in a heterologous background acted as stress tolerance enhancers, makes these genes very attractive tools to induce stress tolerance in any organism of interest, without the need for accessory compounds. The ability of these genes to enhance osmotic stress tolerance in yeast cells when isolated and transfected herein, clearly distinct them from other sugar beet genes that are known to play a role in (other) stress responses, but that were not used in an isolated form. One of these novel sugar beet genes of the present invention encodes a subunit of casein kinase. It was surprising to disclose for the first time a plant casein kinase subunit and more surprisingly an α catalytic subdomain of casein kinase exerting a function in salt stress response. Herein is described a cDNA clone (BvCKA2) encoding one of the catalytic α subunits of sugar beet protein kinase CK2 (formerly casein kinaseII). BvCKA2 increases the tolerance to NaCl of yeast. In addition, it is herein shown that expression of BvCKA2 in sugar beet is induced by salt stress.

Also the identification of two other genes as a sugar beet dihydroorotase and a translation initiation factor 1A, respectively, was very surprising since, in the present state of the art of the plant-stress field, there is no evidence for the function of such proteins as stress tolerance inducers.

Furthermore it was surprising that two of the isolated genes encoded polypeptides for which no homologues could be found. Therefore these genes can be considered as a novel type of genes encoding a novel type of protein that confer to a heterologous organism tolerance to stress.

All these genes of the present invention are cloned in an expressible vector format and are able to contribute agronomically interesting features to a transgenic plant when transfected herein.

To identify novel plant genes involved in NaCl stress, the inventors adopted a strategy previously utilized with the yeast *Saccharomyces cerevisiae* (Serrano, 1996). The inventors constructed a cDNA library from salt-stressed sugar beet and screened it in a salt-sensitive yeast strain. The rational for this screening of plant genes expressed in yeast cells is that some of the molecular mechanisms of yeast salt tolerance are thought to be similar to those of plant cells (Serrano, 1996, Hasegawa et al. 2000b). Sugar beet is a relatively halophytic crop plant (Marschner, 1995) which could be a better source of halotolerance genes than the model plant *Arabidopsis*.

Accordingly, the invention embodies five novel *Beta vulgaris* genes with nucleotide sequences as given in SEQ ID NOs 1 to 5, encoding five different polypeptides with amino acid sequences as given in SEQ ID NOs 6 to 10.

The present invention further relates to vectors, or host cells or organisms comprising at least part of the sequences as set forth in SEQ ID NOs 1 to 5.

Furthermore in another preferred embodiment of the invention, a method is provided for conferring stress tolerance to an organism of interest, preferably plants, yeast or bacteria, comprising the introduction of at least one of the five sugar beet genes in that organism.

DETAILED DESCRIPTION OF THE INVENTION

One of the problems underlying the present invention is to provide genes that can be used to enhance stress tolerance of organisms that suffer from stress conditions like osmotic stress, caused by salt or drought and/or stress conditions like cold, chilling and freezing stress or oxidative stress.

This invention offers solutions to the above-described problem and is disclosed in the following embodiments characterized in the claims.

A solution is achieved by providing a set of genes that are originating from *Beta vulgaris*, a stress tolerant crop plant, that were isolated and that confer to *Saccharomyces cerevisiae* tolerance to stress conditions, for instance genes that confer stress tolerance to the Na+ sensitive yeast strain JM26. Additional to the fact that these genes are all from the same plant, they all showed a salt resistance phenotype when separately transformed to a salt sensitive yeast mutant. By doing so they all acted as a sole enhancer of stress tolerance. Unexpectedly these genes encode proteins with very different putative functions like casein kinase α subunit, dihydroorotase, translation initiation factor 1A and some of them are even of an unknown type. Other features such as the very strong salt resistance phenotype that some of these genes showed in yeast and the fact that some of these genes are frequently isolated in the selective screening procedure in yeast, contribute to the effectiveness and efficiency of these genes as stress tolerance enhancers. This set of genes enables the person skilled in the art to genetically alter the organism of interest in order to make it tolerant to stress situations. For the cultivation of crop plants for example, of which many are sensitive to stress conditions like salt, drought or cold, the disclosed genes offer the possibility to solve the problem of reduced yield and reduced economic profit. Each gene of this set of genes enables the person skilled in the art to modify cell fate and/or plant development and/or plant morphology and/or biochemistry and/or physiology by introducing at least one of these genes into the cell.

Casein kinase, CK2 (formerly CKII), is a serine-threonine protein kinase, ubiquitous and highly conserved among eukaryotic organisms (Glover, 1998). It is composed of two catalytic subunits (α or α') and of two regulatory subunits (β), which tetramerize to adopt an $\alpha_2\beta_2$ structure. Protein kinase CK2 lokalizes both in the nucleus and in the cytoplasmic compartment where it phosphorylates a variety of substrates involved in different cellular functions. In yeast, CK2 is essential and required for at least four biological processes: flocculation, cell cycle progression, cell polarity and ion homeostasis. In plants, CK2 is proposed to be involved in the regulation of cell cycle (Espunya et al. 1999), in the light regulation of plant development (Lee et al. 1999) and in the circadian clock function (Sugano et al. 1998, Suggano et al. 1999). A link between the ectopic expression of plant casein kinase α subunit and stress in general has not been demonstrated previously. Accordingly, the invention relates to a novel nucleic acid of sugar beet as set forth in SEQ ID No. 1, further referred to as clone 154, encoding a casein kinase α catalytic subunit, further referred to as BvCKA2 and capable of enhancing salt tolerance in salt sensitive yeast cells. The open reading frame, starting at nucleotide position 202 and ending at 1203 encodes the BvCKA2 amino acid sequences set forth in SEQ ID NO. 6.

Also the identification of one of the genes as a sugar beet dihydroorotase was very surprising since, in the present state of the art of the plant-stress field, there is no evidence for the function of such an enzyme as a stress tolerance inducer. Accordingly, the invention relates to a novel nucleic acid of sugar beet as set forth in SEQ ID No. 2, further referred to as clone 35, encoding a dihydroorotase, further referred to as BvDHO and capable of enhancing salt tolerance in salt sensitive yeast cells. The open reading frame, starting at nucleotide position 199 and ending at 1236 encodes the BvDHO amino acid sequences set forth in SEQ ID NO:7.

Furthermore the isolation of a translation initiation factor 1A of sugar beet, that acts as a sole stress tolerance enhancer, was very surprising. Although it is known that cells respond to stress by altering the phosphorylation of transcription factors in order to alter the translational capacity, this is the first time that one could demonstrate that a translation factor on its own could contribute in enhancing stress tolerance in an organism when transfected herein.

Accordingly, the invention relates to a novel nucleic acid of sugar beet as set forth in SEQ ID No. 3, further referred to as clone 76, encoding a translation initiation factor 1A, further referred to as BveIF-1A capable of enhancing salt tolerance in salt sensitive yeast cells. The open reading frame, starting at nucleotide position 88 and ending at 521 encodes the BveIF-1A amino acid sequences set forth in SEQ ID NO. 8.

Two other nucleic acids encoded polypeptides with unknown function were found to confer stress tolerance in yeast.

Accordingly, the invention relates to a novel nucleic acid of sugar beet as set forth in SEQ ID No. 4, further referred to as clone 120, encoding a unknown protein, further referred to as Bv120, capable of enhancing salt tolerance in salt sensitive yeast cells. The open reading frame, starting at nucleotide position 29 and ending at 499 encodes the Bv120 amino acid sequences set forth in SEQ ID NO. 9.

Furthermore, the invention relates to a novel nucleic acid of sugar beet as set forth in SEQ ID No. 5, further referred to as clone 20Li, encoding an unknown protein, further referred to as Bv20Li, capable of enhancing salt tolerance in salt sensitive yeast cells. The open reading frame, starting at nucleotide position 1 and ending at 879 encodes the Bv20Li amino acid sequences set forth in SEQ ID NO. 10.

A first aspect of the present invention is the procedure of screening a cDNA library from NaCl-induced sugar beet leaves and subsequent isolation of the five sugar beet genes as mentioned above. A functional approach to identify sugar beet proteins that are involved in the response of plants to salt stress was followed. For this purpose a NaCl-induced cDNA expression library was constructed from sugar beet leaves as described in example 1 and example 3 and the Na$^+$-sensitive yeast mutant strain JM26 (see example 2) was used to screen for sugar beet cDNAs that increased the yeast salt tolerance upon overexpression. The growth of this yeast mutant is normally inhibited at NaCl concentrations (150 mM) similar to those impairing growth of most crop species. This screening procedure is described in example 4. After transforming 100.000 individual cells with the plasmids pYPGE15 containing the cDNA inserts, colonies were pooled and selected for their ability to grow in the presence of 150 mM NaCl (see example 4). Four of the positive clones, were named clone 154, clone 35, clone 76 and clone 120.

The yeast clones 154, clone 35, clone 76 and 120 had a clear salt tolerance phenotype and the phenotype was very reproducible: under 150 mM NaCl control yeast cells did not grow at all, and yeast cells overexpressing the insert 154, 35, 76 or 120 grew. Clones 35 and 76 were selected twice and three times respectively during the selection of salt tolerant yeast clones, suggesting the abundant presence of those clones in the salt stressed sugar beet leaves.

The same selective screening procedure was also performed to select Li$^+$ tolerant yeast cells. After transformation of the sugar beet cDNA library, colonies were pooled and selected for their ability to grow in the presence of 20 mM LiCl without methionine as described in example 4. One of the positive clones was named 20Li. Clone 20Li showed a strong Li$^+$ tolerance phenotype.

The definition of a strong phenotype is based on drop test experiments. Several dilutions of saturated cultures (1:10, 1:100, 1:1000) were made and these were grown on selective media (150 mM NaCl plus methionine or 20 mM LiCl without methionine). Strong phenotypes are those clones that grew well in all the dilutions assayed (e.g. clone 35, 76, 120 for NaCl and clone 20Li for LiCl). Clone 154 had not such a very strong phenotype in yeast because only the first dilution (1:10) was able to grow in selective medium. The control cells expressing the empty plasmid did not grow at all in the selective media. Accordingly, a first embodiment of the present invention relates to a method for induction of stress tolerance in an organism comprising expression of at least one *Beta vulgaris* gene which confers stress tolerance to yeast cells.

In another embodiment, the invention relates to the use of a *Beta vulgaris* nucleic acid for enhancing stress tolerance in a plant comprising expression of said *Beta vulgaris* nucleic acid characterized in that it confers stress tolerance to yeast cells, for instance yeast cells derived from the Na$^+$ sensitive yeast strain JM26.

In a further embodiment, the present invention is a method for induction of osmotic stress tolerance in an organism comprising expression of at least one *Beta vulgaris* gene which confers osmotic or oxidative stress tolerance, such as salt stress or drought stress or frost stress tolerance, to yeast cells.

The expression "induction of stress tolerance" as used herein has the same meaning as "enhancing stress tolerance" and therefore can be used interchangeable.

All the selected clones are hereunder described in more detail. To find possible homologues, the amino acid sequence of the (putative) ORFs were subjected to a homology search, performed with the BlastP 2.0.10 program (Altschul et al. 1997). The cDNA insert of the plasmid present in clone 154 contains a 1527 base pair cDNA (SEQ ID No. 1) with an open reading frame of 999 base pairs encoding a polypeptide of 333 amino acids (SEQ ID NO. 6) with a predicted molecular weight of 39.4 kD. This polypeptide, named BvCKA2, has 91,6% identity with one of the catalytic subunits (alpha chain 2) of the protein kinase CK2 from *Zea mays* (ZMCKA2). BvCKA2 contains the 11 typical subdomains of the eukaryotic protein kinases (Hanks et al. 1995) and all the conserved amino acid residues characteristic of CK2 catalytic subunits (FIG. 1). The 170-DWG-172 present in the catalytic site is an invariant finger-printing pattern for CK2 alpha subunits (Niefind et al. 1998). Also present in BvCKA2 are the essential catalytic lysine 63-K and the highly basic region 69-KKKKIKR-75. The cDNA insert of the plasmid present in clone 35 contains a 1743 base pair cDNA (SEQ ID No. 2) with an open reading frame of 1035 base pairs encoding a polypeptide of 345 amino acids (SEQ ID NO. 7) with a predicted molecular weight of 40.8 kD. This polypeptide, named BvDHO, has 79% identity with the precursor of the protein dihydroorotase from *Arabidopsis thaliana* and has 81% identity with the Dihydroorotase of potato (WO0118190, WO0114569) The cDNA insert of the plasmid present in clone 76 contains a 643 base pair cDNA (SEQ ID No. 3) with an open reading frame of 432 base pairs encoding a polypeptide of 144 amino acids (SEQ ID NO. 8) with a predicted molecular weight of 17 kD. This polypeptide, named BveIF-1A, has 88% identity with the precursor of the eukaryotic translation initiation factor 1A (eIF-1A or formerly known as eiF-4C) from *Onobrychis viciifolia* (common sainfoin). The cDNA insert of the plasmid present in clone 120 contains a 845 base pair cDNA (SEQ ID No. 4) with an open reading frame of 468 base pairs encoding a polypeptide of 156 amino acids (SEQ ID NO. 9), named Bvl20, with a predicted molecular weight of 18.5 kD. The cDNA insert of the plasmid present in clone 20Li contains a 879 base pair cDNA (SEQ ID No. 5) with a putative open reading frame of 876 base pairs encoding a polypeptide of 292 amino acids (SEQ ID NO. 10) with a predicted molecular weight of 34.5 kD. This polypeptide, named Bv20Li, has 59% identity with a predicted protein from a genomic clone of *Arabisopsis thaliana*, for which no function has been described.

In a further embodiment the invention thus relates to the use of a *Beta vulgaris* nucleic acid for enhancing osmotic or oxidative stress tolerance in a plant wherein said *Beta vulgaris* nucleic acid is selected from one of the following:

(a) a nucleic acid comprising a DNA sequence as given in any of SEQ ID NOs 1 to 5 or the complement thereof, (b) a nucleic acid comprising the RNA sequence corresponding to any of SEQ ID NOs 1 to 5 or the complement thereof, (c) a nucleic acid specifically hybridizing to the nucleic acid of (a) or (b) under high stringency conditions, (d) a nucleic acid encoding a protein with an amino acid sequence which is at least 93%, preferably at least 95%, 96%, 97%, 98% or 99% identical to the amino acid sequence as given in SEQ ID NO 6, (e) a nucleic acid encoding a protein with an amino acid sequence which is at least 80%, preferably at least 82%, 85% or 90%, more preferably at least 95%, 98% or 99%% identical to the amino acid sequence as given in SEQ ID NO 7, (f) a nucleic acid encoding a protein with an amino acid sequence which is at least 89%, preferably 90%, 92%, 95% or 96%, more preferably 97%, 98% or 99% identical to the amino acid sequence as given in SEQ ID NO 8, (g) a nucleic acid encoding a protein with an amino acid sequence which is at least 75%, preferably 80%, 85% or 90%, more preferably 95%, 96%, 97%, 98% or 99% identical to the amino acid sequence as given in SEQ ID NO 9, (h) a nucleic acid encoding a protein with an amino acid sequence which is at least 65%, preferably 70%, 75%, 80%, 85% or 90%, more preferably 95%, 96%, 97%, 98% or 99% identical to the amino acid sequence as given in SEQ ID NO 10, (i) a nucleic acid encoding a protein comprising the amino acid sequence as given in any of SEQ ID NOs 6 to 10, (j) a nucleic acid encoding an immunologically active and/or functional fragment of a protein encoded by a DNA sequence as given in any of SEQ ID NOs 1 to 5, (k) a nucleic acid which is degenerated to a nucleic acid as given in any of SEQ ID NOs 1 to 5, or which is degenerated to a nucleic acid as defined in any of (a) to (j) as a result of the genetic code, (l) a nucleic acid which is diverging from a nucleic acid encoding a protein as given in any of SEQ ID NOs 6 to 10, or which is diverging from a nucleic acid as defined in any of (a) to (j) as a result of differences in codon usage between organisms, (m) a nucleic acid which is diverging from a nucleic acid encoding a protein as given in any of SEQ ID NOs 6 to 10, or which is diverging from a nucleic acid as defined in any of (a) to (j) as a result of differences between alleles, and (n) a nucleic acid as defined in any one of (a) to (m) characterized in that said nucleic acid is DNA, cDNA, genomic DNA or synthetic DNA.

Furthermore, one of the embodiments of this invention is a method for enhancing stress tolerance in a plant or in plants comprising expression of at least one of the nucleic acids as described above in cells, tissues or parts of said plant or plants. Also for those plants that already express a nucleic acid according to the invention, another embodiment of the present invention is a method for altering stress tolerance in said plants comprising altering the expression of a nucleic acid of the invention in cells, tissues or parts of said plants.

In an interesting embodiment the present invention relates to a method for induction of stress tolerance in an organism, for instance a plant, comprising the expression or altering the expression of a of a nucleic acid encoding a casein kinase alpha subunit, for instance a plant casein kinase alpha subunit in cells, tissues or parts of said organism. More preferably the present invention relates to a method for induction of osmotic, salt, Na+ or Li+ stress tolerance to an organism, e.g. a plant, yeast or bacteria, comprising the expression of a plant casein kinase α subunit, such as a casein kinase α subunit of sugar beet or a homologue or an orthologue thereof. In a preferred embodiment the present invention relates to a method for the induction of Na+ tolerance in a plant, such as rice, comprising the expression of a casein kinase α subunit of sugar beet.

In an interesting embodiment of the invention, said plant casein kinase α subunit is represented by SEQ ID Nos 1 and 6.

According to another embodiment the invention relates to the use of a casein kinase to control the flowering process of plants. The present inventors surprisingly found that overexpression of a casein kinase α subunit, such as the sugar beet casein kinase α subunit identified in the present invention has an effect on the flowering process, independent from the light.

The invention thus relates to a method for controlling the process of flowering of a plant comprising the expression or altering the expression of a nucleic acid encoding a casein kinase alpha subunit, such as represented by SEQ ID NO 6 in cells, tissues or parts of said plant.

The invention thus also relates to the use of a nucleic acid encoding a casein kinase alpha subunit, such as represented by SEQ ID NO 6 for controlling the process of flowering of a plant.

Even so a preferred embodiment of the present invention relates to a method for enhancing stress tolerance in an organism, for instance in a plant, comprising the expression or altering the expression of a nucleic acid encoding a dihydroorotase in cells, tissues or parts of said organism or said plant.

More preferably the present invention relates to a method for induction of osmotic, salt, Na+ or Li+ stress tolerance in an organism, e.g. a plant, yeast or bacteria, comprising the expression of a plant dihydroorotase, such as dihydroorotase of sugar beet or a homologue or an orthologue or a paralogue thereof. In a preferred embodiment, the present invention relates to a method for the induction of Na+ tolerance to a plant, such as rice, comprising the expression of the dihydroorotase of sugar beet. In an interesting embodiment of the invention, said dihydroorotase is represented by SEQ ID Nos 2 and 7. In another embodiment the present invention relates to a method for induction of stress tolerance in an organism, for instance in a plant, comprising the expression or altering the expression of a nucleic acid encoding a translation initiation factor 1A in cells, tissues or parts of said organism. More preferably the present invention relates to a method for induction of osmotic, salt, Na+ or Li+ stress tolerance in an organism, e.g. a plant, yeast or bacteria, comprising the expression of a plant translation initiation factor 1A, such as a translation initiation factor 1A of sugar beet or a homologue, an orthologue or a paralogue thereof. In a preferred embodiment of the present invention relates to a method for the induction of Na+ tolerance in a plant, such as rice, comprising the expression of a translation initiation factor 1A of sugar beet. In an interesting embodiment of the invention, said translation initiation factor 1A is represented by SEQ ID Nos 3 and 8.

In another embodiment the present invention relates to a method for enhancing stress tolerance in a plant comprising the expression of or altering the expression of a nucleic acid as represented by SEQ ID NO 4 or 5, or a homologue, an orthologue or a paralogue thereof.

The present invention also relates to an isolated nucleic acid encoding a protein or an immunologically active and/or functional fragment of such a protein selected from the group consisting of:

(a) a nucleic acid comprising a DNA sequence as given in any of SEQ ID NOs 1 to 5 or the complement thereof, (b) a nucleic acid comprising the RNA sequences corresponding to any of SEQ ID NOs 1 to 5 or the complement thereof, (c) a nucleic acid specifically hybridizing to the nucleotide sequence as defined in (a) or (b) under high stringency conditions, (d) a nucleic acid encoding a protein with an amino acid sequence which is at least 93%, preferably at least 95%, 96%, 97%, 98% or 99% identical to the amino acid sequence as given in SEQ ID NO 6, (e) a nucleic acid encoding a protein with an amino acid sequence which is at least 80% preferably at least 82%, 85% 86%, 87%, 88%, 89%, 90%, 91%, 92%, 93%, 94%, 95%, 96%, 97%, 98% or 99% identical to the amino acid sequence as given in SEQ ID NO 7, (f) a nucleic acid encoding a protein with an amino acid sequence which is at least 89%, preferably at least 90%, 91%, 92%, 93%, 94%, 95%, 96%, 97%, 98% or 99% identical to the amino acid sequence as given in SEQ ID NO 8, (g) a nucleic acid encoding a protein with an amino acid sequence which is at least 75% preferably at least 78%, 80%, 85%, 87%, 89%, 91%, 93%, 96%, 95%, 97%, 98% or 99% identical to the amino acid sequence as given in SEQ ID NO 9, (h) a nucleic acid encoding at least part of a protein with an amino acid sequence which is at least 65% preferably at least 70%, 75%, 80%, 85%, 90%, 95%, 96%, 97%, 98% or 99% identical to the amino acid sequence as given in SEQ ID NO 10, (i) a nucleic acid encoding a protein comprising the amino acid sequence as given in any of SEQ ID NOs 6-10, (j) a nucleic acid encoding an immunologically active and/ or functional fragment of a protein encoded by a DNA sequence as given in any of SEQ ID NOs 1 to 5, (k) a nucleic acid which is degenerated to a nucleic acid as given in any of SEQ ID NOs 1 to 5, or which is degenerated to a nucleic acid as defined in any of (a) to (j) as a result of the genetic code, (l) a nucleic acid which is diverging from a nucleic acid encoding a protein as given in any of SEQ ID NOs 6 to 10, or which is diverging from a nucleic acid as defined in any of (a) to (j) as a result of differences in codon usage between organisms, (m) a nucleic acid which is diverging from a nucleic acid encoding a protein as given in any of SEQ ID NOs 6 to 10, or which is diverging from a nucleic acid as defined in any of (a) to (j) as a result of differences between alleles, and (n) a nucleic acid as defined in any one of (a) to (m) characterized in that said nucleic acid is DNA, cDNA, genomic DNA or synthetic DNA.

The clone 154 (SEQ ID NO 1) was chosen for further characterization because it has homologues in yeast. Many information is available about CK2 in yeast and other organisms e.g. mutants of the yeast CK2 subunits.

In order to confirm the presence of BvCKA2 in the sugar beet genome and to estimate the number of genes encoding the CK2 catalytic subunits in this plant species, the inventors performed a Southern blot analysis. As described in example 8 we first hybridized the genomic sugar beet genomic DNA using a fragment including the ORF of BvCKA2 (FIG. 2A). The presence of several hybridization fragments in all lanes independent of the restriction endonucleases used to digest the genomic DNA, suggest that CKA2 is a member of a multicopy gene family in sugar beet. The hybridization probe we used may recognize all the members of the CK2 family, including genes coding for different isoforms of the catalytic subunit. When a more specific probe was used for hybridization, only two bands in the BamHI and HindIII digest, and one band in the EcoRI digest could be detected (FIG. 2B). This may indicate the presence of two very closely related genes coding for CK2 catalytic subunits in sugar beet.

To confirm the functionality of the BvCKA2 gene to confer stress tolerance to yeast, the complementation of the yeast CK2 mutation was demonstrated (example 6).

Figure 3:
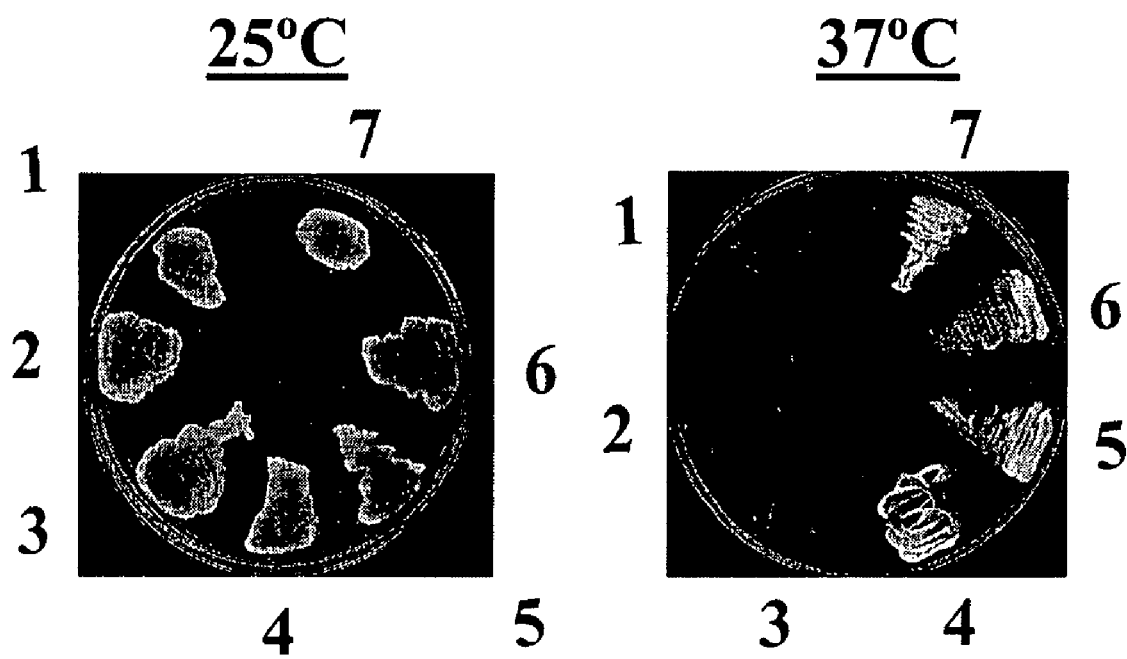

In the yeast *Saccharomyces cerevisiae*, CK2 is essential for growth and there are two redundant genes, CKA1 and CKA2, encoding two related catalytic subunits (Padmanabha et al. 1990). YDH8 is a cka1/cka2 double mutant yeast strain that carries a plasmid with a thermosensitive cka2 subunit (pDH8). To determine whether BvCKA2 could suppress the thermosensitive phenotype of YDH8 strain, we transformed YDH8 cells with the plasmid pYPGE15+BvCKA2. While the YDH8 strain could only grow at the permissive temperature of 25° C., YDH8 overexpressing BvCKA2 was able to grow at 25° and at 37° C. (FIG. 3). BvCKA2 could also complement other phenotypic characteristics of the cka1,2 mutant strain such as flocculation (data not shown). Finally, when the pDH8 plasmid was removed and the cells only expressed BvCKA2, the plant enzyme could support yeast growth at 25° and 37° C. (data not shown). These results clearly suggest that BvCKA2 can functionally replace the yeast catalytic subunit of CK2 and this may suggest that CK2 is regulating related processes in both organisms According to these aspects of the invention, that illustrate the cloning of the BvCKA2 gene, the present invention refers to a nucleic acid molecule of at least 15 nucleotides in length specifically hybridizing with a nucleic acid of the invention.

In an a related preferred embodiment, the present invention also refers to nucleic acid molecule of at least 15 nucleotides in length specifically amplifying a nucleic acid of the invention.

Another preferred embodiment of the present invention is a vector comprising a nucleic acid sequence as defined above, such as an expression vector wherein the nucleic acid sequence is operably linked to one or more control sequences allowing the expression of said sequence in prokaryotic and/or eukaryotic host cells.

A further related embodiment of the present invention is a host cell containing a nucleic acid molecule as defined above or a vector as described above, such host cell for example being a bacterial, insect, fungal, plant or animal cell.

The functionality of the BvCKA2 gene was also confirmed by the demonstration of growth of a Na+ sensitive yeast strain JM26 (example 2) in media with NaCl as described in example 7.

Figure 4:
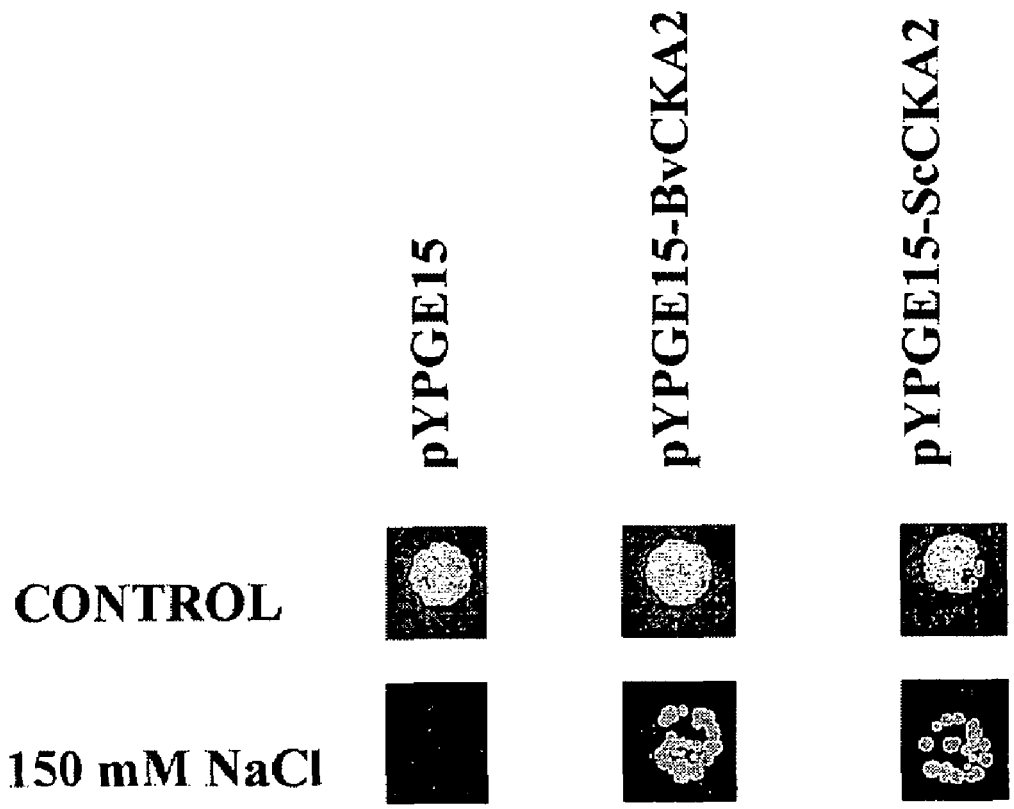

This yeast mutant, defective in the non-essential β regulatory subunit of CK2, displays a phenotype of hypersensitivity to $Na^+$ and $Li^+$ (Bidwai et al. 1995, Nadal et al. 1999b). Overexpression of both the sugar beet catalytic alpha 2 subunit (BvCKA2) as well as one of the yeast catalytic subunits (ScCKA2), that was cloned as described in example 5, increased the $Na^+$ tolerance of the JM26 yeast cells (FIG. 4). This indicates a specific effect of CK2 on Na+ tolerance. The increased Na+ tolerance of yeast cells overexpressing BvCKA2 could also be demonstrated in liquid cultures. The above mentioned functional effects of overexpression of the sugar beet genes can possibly also be obtained by applying the isolated polypeptides produced by those genes or produced in a synthetic way.

Therefore, the present invention also relates to an isolated polypeptide encodable by a nucleic acid of the present invention as described above, or a homologue or a derivative thereof, or an immunologically active and/or functional fragment thereof, this polypeptide preferably having an amino acid sequence as given in any of SEQ ID NO 6-10, or a homologue or a derivative thereof, or an immunologically active and/or functional fragment thereof.

Also a related preferred embodiment of the present invention is a method for producing a polypeptide as mentioned above comprising culturing a host cell as mentioned above, under conditions allowing the expression of the polypeptide and recovering the produced polypeptide from the culture.

Also the functional effects that were seen upon expression of the sugar beet genes could be influenced by proteins that bind to the polypeptides produced by those genes. Therefore, in yet another preferred embodiment, the present invention relates to an antibody specifically recognizing a polypeptide as mentioned above or a specific epitope of said polypeptide.

In order to investigate whether the mechanism of salt tolerance conferred by BvCKA2 was due to the regulation of ion homeostasis, the intracellular levels of $Na^+$ and $K^+$ in cells growing in the presence of these ions (Table 1) was determined as described in example 7. It was determined that expression of BvCK42 did not significantly change the $Na^+$ and $K^+$ content in yeast cells.

TABLE 1

Potassiun and sodium content (mM) of JM26 cells overexpressing CKA2. Cells were grown overnight in the presence of 75 mM NaCl. Results are the mean of three independent experiments ± SD.

|  | [K] | [Na] |
|---|---|---|
| PYPGE15 | 57 ± 11 | 136 ± 9 |
| PYPGE15 + BvCKA2 | 56 ± 3 | 146 ± 9 |

In yeast, it has been shown that mutants in the β regulatory subunit of the CK2 (CKB1) are highly sensitive to $Na^+$ and $Li^+$ (Bidwai et al. 1995, Nadal et al. 1999a). An aspect of the present invention is that overexpression of not only the yeast but also the plant CK2 α catalytic subunit increases yeast tolerance to Na⁺. Since not only reduction of CK2 activity increases sensitivity to NaCl (ckb1 yeast mutants) but also increase in CK2 activity improves salt tolerance, it is possible that CK2 is an important determinant of salt tolerance in yeast. However, the mechanism by which CK2 may regulate yeast salt tolerance is not known. Recently published data suggest that CK2 regulated the transcription of the ENA1 ATPase (Teney and Glover, 1999), the main determinant for Na⁺ efflux in yeast. One of the aspects of the invention teaches away from this, since it was demonstrated that the salt tolerance conferred by BvCKA2 is not related to the regulation of the Na⁺ homeostasis within the cells. Furthermore is was shown that overexpression of BvCKA2 improved the salt tolerance of the JM26 yeast mutant lacking the two major transport systems involved in the Na⁺ efflux (the ENA1-4 ATPase and the Na⁺/H⁺ antiporter NHA1). In addition, measurements of intracellular Na⁺ and K⁺ did not show any significant difference between controls and cells overexpressing CKA2 (Table 1). Yeast cells lacking the vacuolar Na⁺/H⁺ antiporter NHX also showed improved growth in media with NaCl when they overexpressed CKA2 (data not shown) ruling out the possibility that CK2 alters the cytoplasmic levels of Na⁺ through vacuolar sequestration. According to this, Nadal et al. (1999b) showed that the salt sensitivity of the yeast ckb1 mutant was not due to defects in the fluxes of sodium. These authors postulated that CK2 might reduce, by phosphorylation, the Na⁺ sensitivity of an important component of the cellular machinery that is salt sensitive. It is difficult to find such putative targets of salt toxicity since many substrates including transcription factors, protein kinases and topoisomerases have been found to posses putative CK2 phosphorylation sites (Grein et al. 1999).

Figure 5:
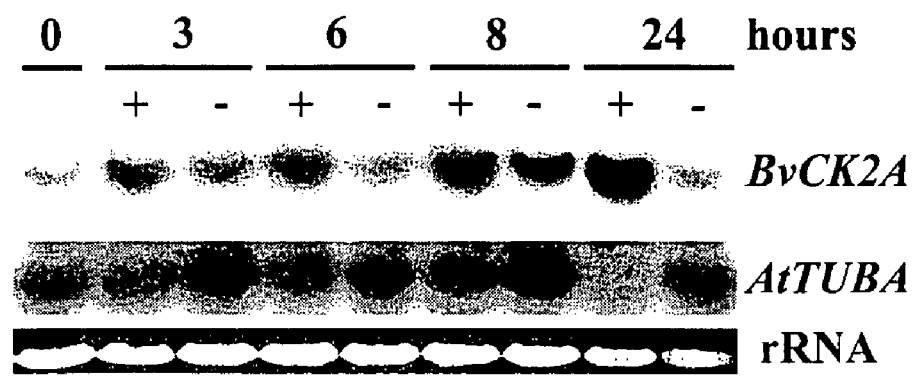

In order to confirm that BvCKA2 participates in the response of sugar beet plants to salt stress the accumulation of BvCKA2 mRNA in response to various exposure times to NaCl was analyzed. RNA gel blot using a CKA2 specific probe showed only one band that corresponded to the size of the BvCKA2 cDNA (1.5 Kb). As shown in FIG. 5 the BvCKA2 mRNA accumulated with time upon NaCl treatment, and reached a maximum at 24 hours. The increase was about 3-fold as compared to control plants. It is interesting to note that the sugar beet cDNA library used to search for genes that are involved in stress tolerance was also obtained from plants treated for 24 hours with NaCl.

In order to confirm that BveIF-1A participates in the response of yeast cells to salt stress the incorporation of phenylalanin in proteins was measured. The inventors observed that under salt stress conditions the incorporation of phenylalanin in yeast cells transformed with the cDNA encoding BveIF-1A was much higher than in cells transformed with the empty vector (example 12). These results demonstrate that eIF-1a is directly involved in the response to stress tolerance. Furthermore these results show that overexpression of this cDNA (according to SEQ ID No. 3) can improve translation under salt stress condition. These new findings are very interesting since this is the first evidence showing that a translation initiation factor improves stress tolerance.

The sugar beet genes of the present invention were shown to confer stress tolerance to a heterologous yeast when transfected herein.

Furthermore, the sugar beet genes of the present invention were shown to confer stress tolerance to a plant when transfected herein (see example 10).

A further and agronomically interesting application of these genes, is to transfect them into a crop plant in order to render this crop more tolerant to unfunate growth conditions. Rice plants can be transfected with at least one of the sugar beet genes of the present invention (example 9), which can confer salt tolerance to the rice plants. This application offers a solution to the reduced yield of rice in heavily irrigated lands, caused by the deposition and accumulation of salts from the irrigation water in the soil.

According to the above mentioned aspects of the invention, documenting the effect of the sugar beet gene in a physiologic response to a stress situation in planta, the present invention also relates to a method for the production of transgenic plants, plant cells or plant tissues comprising the introduction of a nucleic acid molecule as defined above in an expressible format or a vector as defined above in said plant, plant cell or plant tissue.

Also within the scope of the present invention is a method for the production of altered plants, plant cells or plant tissues comprising the introduction of a polypeptide of the present invention directly into a cell, a tissue or an organ of said plant.

In a further embodiment the present invention relates to a method for enhancing stress tolerance in a plant cell, tissue or plant comprising the introduction of any nucleic acid as mentioned above into said plant cell, tissue or organ of said plant.

Furthermore, the present invention provides in a preferred embodiment for a method to effect the expression of a polypeptide as mentioned above comprising the introduction of a nucleic acid molecule of the present invention, optionally operably linked to one or more control sequences or a vector as defined above stably into the genome of a plant cell. Even so in a related embodiment, the invention provides for a method as described here above, further comprising regenerating a plant from said plant cell.

In a further embodiment, the invention here disclosed, relates to a transgenic plant cell comprising a nucleic acid sequence of the invention which is operable linked to regulatory elements allowing transcription and/or expression of said nucleic acid in plant cells or a transgenic plant cell obtainable by a method as described above. Furthermore, this transgenic plant cell can have said nucleic acid of the invention stably integrated into its genome. Also in the scope of the present invention is a transgenic plant or plant tissue comprising plant cells as described above, and furthermore this transgenic plant can display increased tolerance to stress, preferably osmotic stress such as salt, Na+, Li+, drought, cold or freezing stress or oxidative stress, compared to the corresponding wild type plant. A related embodiment of the present invention is a harvestable part of such a plant which can be selected from the group consisting of seeds, leaves, fruits, stem cultures, rhizomes and bulbs or the progeny derived from any of the plants or plant parts as described above.

Because it was demonstrated that the sugar beet genes of the present invention are not functionally restricted to their homologous background, the scope of the present invention also refers to a method for altering stress tolerance in (a) organism(s) comprising the expression or altering the expression of a nucleic acid of the invention in cells, tissues or parts of said organism(s).

As known by the person skilled in the art, many genes involved in salt stress are also involved in responses to other stress situations. Accordingly, the present invention also relates to above mentioned methods for producing transgenic cells, plants or other organisms, wherein said stress can be osmotic stress, salt stress, drought stress, freezing stress or cold stress or oxidative stress.

In most practical applications of the present invention, the novel technology will be used to create a beneficial effect for the transformed organism. Therefore in a most preferred embodiment, the present invention relates to a method according to any of the methods as mentioned above, said method leading to an increase in yield and even so to a method wherein said expression of said nucleic acid occurs under the control of a promoter. Said promoter can be a constitutive or inducible promoter. In cases where cell-specific, tissue-specific or organ-specific expression of genes is envisaged, a cell-specific, tissue-specific or organ-specific promoter is used. An exhaustive but non-limiting list of examples of promoters that can be used in the methods of the invention is provided in Table 4.

As for yeast, many interacting partners for the plant CK2 have been postulated, including transcription factors, such as CCA1 involved in regulation of the circadian clock (Sugano et al. 1999), or GBF1 that regulates the expression of light inducible genes (Donald and Cashmore 1990). Interestingly, two protein kinases induced by salt stress, ATPK19 and ATPK6, also contain putative CK2 phosphorylation sites (Mizoguchi et al. 1995).

Accordingly, a preferred embodiment of the present invention is a method for identifying and obtaining proteins interacting with a polypeptide of the present invention comprising a screening assay wherein a polypeptide of the present invention is used. This method could for example comprise a two-hybrid screening assay wherein a polypeptide of the present invention as a bait and a cDNA library as prey are used.

Also a method for modulating the interaction between a polypeptide of the present invention and interacting protein partners obtainable by a method as described above is in the scope of the present invention. Furthermore, the present invention embodies a method for identifying and obtaining compounds interacting with a polypeptide of the present invention comprising the steps of:

(a) providing a two-hybrid system wherein a polypeptide of the present invention and an interacting protein partner obtainable by a method as described above are expressed,
(b) interacting said compound with the complex formed by the expressed polypeptides as defined in a), and,
(c) performing measurement of interaction of said compound with said polypeptide or the complex formed by the expressed polypeptides as defined in (a).

Even so, the present invention embodies a method for identifying compounds or mixtures of compounds which specifically bind to a polypeptide of the present invention, comprising:

(a) combining a polypeptide of the present invention with said compound or mixtures of compounds under conditions suitable to allow complex formation, and,
(b) detecting complex formation, wherein the presence of a complex identifies a compound or mixture of compounds which specifically binds said polypeptide.

Because these interaction partners of the polypeptide of the present invention can cooperate in the functionality of these polypeptides, the present invention also embodies the use of a compound or mixture of compounds identified by means of a method as described above as a factor that enhances stress tolerance in (a) organism(s).

Accordingly, the present invention embodies the use of a nucleic acid molecule of the invention as defined above, a vector of the invention, a polypeptide of the invention for increasing yield or for stimulating plant growth. In particular the present invention offers the opportunity to increase the yield of any harvestable part of a plant, such as root, leaf, seeds etc.

It is important for the agronomic success of a crop to be able to cope with stress situations. Therefore it could be useful to use the genes or the polypeptides of the present invention to screen important crops for the presence of stress tolerance genes. Accordingly the present invention relates to a diagnostic composition comprising at least a nucleic acid of the invention, a vector of the invention, a polypeptide of the invention or an antibody of the invention.

It is described that in normal plant growing conditions there is a typically low concentration of less than 1 mM Na+. Therefore the present invention offers the possibility to use a plant obtainable by the method as defined above or the plant of the invention for culturing on soil with a salt content of more than 1 mM ions. In most experiments it was shown that salt tolerant plants were able to grow on in conditions with about 40 mM to about 400 mM Na+.

DEFINITIONS AND ELABORATIONS TO THE EMBODIMENTS

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.), acylation and radiolabels (e.g. $^{125}$I, $^{131}$I, $^{35}$S, $^{14}$C, $^{32}$P, $^{33}$P, $^{3}$H) as well as non-naturally occurring amino acid residues, L-amino acid residues and D-amino acid residues.

"Homologues" or "Homologs" of a protein of the invention are those peptides, oligopeptides, polypeptides, proteins and enzymes which contain amino acid substitutions, deletions and/or additions relative to the said protein with respect to which they are a homologue without altering one or more of its functional properties, in particular without reducing the activity of the resulting product. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 2.

TABLE 2

Properties of naturally occurring amino acids.

| Charge properties/ hydrophobicity | Side group | Amino Acid |
| --- | --- | --- |
| nonpolar hydrophobic | aliphatic | ala, ile, leu, val |
| | aliphatic, S-containing | met |
| | aromatic | phe, trp |
| | imino | pro |
| polar uncharged | aliphatic | gly |
| | amide | asn, gln |
| | aromatic | tyr |
| | hydroxyl | ser, thr |
| | sulfhydryl | cys |
| positively charged | basic | arg, his, lys |
| negatively charged | acidic | asp, gly |

Two special forms of homology, orthologous and paralogous, are evolutionary concepts used to describe ancestral relationships of genes. The term "paralogous" relates to gene-duplications within the genome of a species leading to paralogous genes. The term "orthologous" relates to homologous genes in different organisms due to ancestral relationship. The present invention thus also relates to homologues, paralogues and orthologues of the genes and proteins of the invention. The paralogues or orthologues of the genes and proteins of the invention may have a lesser percentage of sequence identity with the sequences or proteins of the invention than the strictly interpreted "homologues" as defined earlier.

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

Insertional amino acid sequence variants of a protein of the invention are those in which one or more amino acid residues are introduced into a predetermined site in said protein. Insertions can comprise amino-terminal and/or carboxy-terminal fusions as well as intrasequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides including the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope: (EETARFQPGYRS) (SEQ ID NO:22), c-myc epitope: (EQKLISEEDL) (SEQ ID NO:23), FLAG®-epitope: DYKDDDK (SEQ ID NO: 24), lacZ, CMP (calmodulin-binding peptide), HA epitope: YPYDVPDYA (SEQ ID NO: 25), protein C epitope: EDQVDPRLIDGK (SEQ ID NO: 26), and VSV epitope: YTDIEMNRLGK (SEQ ID NO: 27). Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins, which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols. Another alternative to manipulate DNA sequences to produce variant proteins, which manifest as substitutional, insertional or deletional variants comprises targeted in vivo gene modification which can be achieved by chimeric RNA/DNA oligonucleotides as described by e.g. (Palmgren 1997; Yoon et al. 1996).

"Derivatives" of a protein of the invention are those peptides, oligopeptides, polypeptides, proteins and enzymes which may comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection. A derivative of a protein retains the biological or enzymatical activity of the protein where it is derived from.

With "immunologically active" is meant that a molecule or specific fragments thereof such as epitopes or haptens are recognised by, i.e. bind to antibodies.

In the context of the current invention are also included homologous, derivatives and/or immunologically active fragments of any of the inventive sugar beet polypeptides or homologue, derivative or fragment thereof as defined supra.

"Antibodies" include monoclonal, polyclonal, synthetic or heavy chain camel antibodies as well as fragments of antibodies such as Fab, Fv or scFv fragments. Monoclonal antibodies can be prepared by the techniques as described previously e.g. (Liddle & Cryer 1991) which comprise the fusion of mouse myeloma cells to spleen cells derived from immunised animals. Furthermore, antibodies or fragments thereof to a molecule or fragments thereof can be obtained by using methods as described in e.g. (Harlow & Lane 1988). In the case of antibodies directed against small peptides such as fragments of a protein of the invention, said peptides are generally coupled to a carrier protein before immunisation of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase, gold spheres and radiolabels (e.g. $^{125}I$, $^{131}I$, $^{35}S$, $^{14}C$, $^{32}P$, $^{33}P$, $^{3}H$). Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins e.g. (Magyar et al. 1997) and immunolocalization. Other uses of antibodies and especially of peptide antibodies include the study of proteolytic processing (Loffler et al. 1994; Woulfe et al. 1994), determination of protein active sites (Lerner 1982), the study of precursor and post-translational processing (Baron & Baltimore 1982; Lerner et al. 1981; Semler et al. 1982), identification of protein domains involved in protein-protein interactions (Murakami et al. 1992) and the study of exon usage in gene expression (Tamura et al. 1991).

In the scope of the current invention are also antibodies recognising the inventive sugar beet polypeptides, derivative or fragment thereof as defined supra.

The terms "gene(s)", "polynucleotide(s)", "nucleic acid sequence(s)", "nucleotide sequence(s)", "DNA sequence(s)" or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analogue such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3'dA (cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU and radiolabels (e.g. $^{125}$I, $^{131}$I, $^{35}$S, $^{14}$C, $^{32}$P, $^{33}$P, $^3$H). Said terms also encompass peptide nucleic acids (PNAs), a DNA analogue in which the backbone is a pseudopeptide consisting of N-(2-aminoethyl)-glycine units rather than a sugar. PNAs mimic the behaviour of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. With "recombinant DNA molecule" or "chimeric gene" is meant a hybrid DNA produced by joining pieces of DNA from different sources. With "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. "Sense strand" refers to the strand of a double-stranded DNA molecule that is homologous to a mRNA transcript thereof. The "anti-sense strand" contains an inverted sequence, which is complementary to that of the "sense strand".

A "coding sequence" or "open reading frame" or "ORF" is defined as a nucleotide sequence that can be transcribed into mRNA and/or translated into a polypeptide when placed under the control of appropriate regulatory sequences, i.e. when said coding sequence or ORF is present in an expressive format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences. Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a give gene, or of the degeneracy of the genetic code or of differences in codon usage. Thus, as indicated in Table 3, amino acids such as methionine and tryptophan are encoded by a single codon whereas other amino acids such as arginine, leucine and serine can each be translated from up to six different codons. Differences in preferred codon usage are illustrated below for *Agrobacterium tumefaciens* (a bacterium), *Arabidopsis thaliana*, *M. Sativa* (two dicotyledonous plants) and *Oryza sativa* (a monocotyledonous plant). These examples were extracted from the web site kazusa.or.jp/codon.com. To give one example, the codon GGC (for glycine) is the most frequently used codon in *Agrobacterium tumefaciens* (36.2%), is the second most frequently used codon in *Oryza sativa* but is used at much lower frequencies in *Arabidopsis thaliana* and *M. sativa* (9% and 8.4%, respectively). Of the four possible codons encoding glycine (see Table 3), said GGC codon is most preferably used in *Agrobacterium tumefaciens* and *Oryza sativa*. However, in *Arabidopsis thaliana* this is the GGA (and GGU) codon whereas in *M. sativa* this is the GGU and (GGA) codon. Allelic variants are further defined as to comprise single nucleotide polymorphisms (SNPs) as well as small insertion/deletion polymorphisms (INDELs; the size of INDELs is usually less than 100 bp). SNPs and INDELs form the largest set of sequence variants in naturally occurring polymorphic strains of most organisms. They are helpful in mapping genes and discovery of genes and gene functions. They are furthermore helpful in identification of genetic loci, e.g. plant genes, involved in determining processes such as growth rate, plant size and plant yield, plant vigor, disease resistance, stress tolerance etc.

TABLE 3

Degeneracy of the genetic code.

| Amino Acid | Three-letter code | One-letter code | Possible codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |

TABLE 3-continued

Degeneracy of the genetic code.

| Aspartic Acid | Asp | D | GAC GAU |
| --- | --- | --- | --- |
| Cysteine | Cys | C | UGC UGU |
| Glutamic Acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

| Possible "STOP" codons |
| --- |
| UAA UAG UGA |

Many techniques are nowadays available to identify SNPs and/or INDELs including (i) PCR followed by denaturing high performance liquid chromatography (DHPLC; e.g. Cho et al. 1999); (ii) constant denaturant capillary electrophoresis (CDCE) combined with high-fidelity PCR (e.g. Li-Sucholeiki et al. 1999); (iii) denaturing gradient gel electrophoresis (e.g. Fischer and Lerman 1983); (iv) matrix-assisted laser desorption/ionization time-of-flight mass spectrometry (MALDI-TOF MS; e.g. Ross et al. 2000); (v) real-time fluorescence monitoring PCR assays (e.g. Tapp et al. 2000); (vi) Acrydite™ gel technology (e.g. Kenney et al. 1998); (vii) cycle dideoxy fingerprinting (CddF; e.g. Langemeier et al. 1994); (viii) single-strand conformation polymorphism (SSCP) analysis (e.g. Vidal-Puig and Moller 1994) and (ix) mini-sequencing primer extension reaction (e.g. Syvanen 1999). The technique of 'Targeting Induced Local Lesions in Genomes' (TILLING; McCallum et al. 2000a,b), which is a variant of (i) supra, can also be applied to rapidly identify an altered gene in e.g. chemically mutagenized plant individuals showing interesting phenotypes.

"Hybridisation" is the process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described e.g. (Sambrook et al.

1989) but the skilled craftsman will appreciate that numerous different hybridisation conditions can be designed in function of the known or the expected homology and/or length of the nucleic acid sequence. With specifically hybridising is meant hybridising under stringent conditions. Sufficiently low stringency hybridisation conditions are particularly preferred to isolate nucleic acids heterologous to the DNA sequences of the invention defined supra. Elements contributing to said heterology include allelism, degeneration of the genetic code and differences in preferred codon usage as discussed supra.

Accordingly, the current invention is also related to the use of the inventive DNA sequences encoding the inventive sugar beet polypeptides, homologue, derivative and/or immunologically fragment thereof as defined higher in any method of hybridisation. The current invention furthermore also relates to DNA sequences hybridising to said inventive DNA sequences.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns, mobilizable DNA sequences such as transposons and DNA tags such as e.g. a T-DNA. With "mobilizable DNA sequence" is meant any DNA sequence that can be mobilised as the result of a recombination event.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding the inventive sugar beet polypeptides or a homologue or derivative thereof or an immunologically active thereof as defined supra.

With "vector" or "vector sequence" is meant a DNA sequence, which can be introduced in an organism by transformation and can be stably maintained in said organism. Vector maintenance is possible in e.g. cultures of *Escherichia coli, Agrobacterium tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognised by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory sequences enabling the creation of an expressible format for the inserted non-vector sequence(s), thus allowing expression of the protein encoded by said non-vector sequence(s). Expression vectors are known in the art enabling protein- (gene-) expression in organisms including bacteria (e.g. *Escherichia coli*), fungi (e.g. *Saccharomyces cerevisiae, Schizosaccharomyces pombe, Pichia pastoris*), insect cells (e.g. baculoviral expression vectors), animal cells (e.g. COS or CHO cells) and plant cells (e.g. potato virus X-based expression vectors, see e.g. Vance et al. 1998—WO9844097). The current invention clearly includes any vector or expression vector comprising a non-vector DNA sequence encoding the inventive sugar beet polypeptides, homologue, derivative and/or immunologically active fragment thereof as defined supra.

As an alternative to (expression) vector-mediated protein production in biological systems, chemical protein synthesis can be applied. Synthetic peptides can be manufactured in solution phase or in solid phase. Solid phase peptide synthesis (Merrifield, 1963) is, however, the most common way and involves the sequential addition of amino acids to create a linear peptide chain. Solid phase peptide synthesis includes cycles consisting of three steps: (i) immobilisation of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl-Z), 2,4,5-trichlorophenyl, 2-bromobenzyloxycarbonyl (Br-Z), tripheylmethyl (Trityl, Trt), and 2,5,7,8-pentamethyl-chroman-6-sulphonyl (Pmc). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidised and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (iodoacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory sequences including a promoter, preferably a plant-expressible promoter, and a terminator sequence.

"Regulatory sequence" refers to control DNA sequences, which are necessary to affect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and enhancers or silencers. The term "control sequence" is intended to include, at a minimum, all components the presence of which are necessary for expression, and may also include additional advantageous components which determines when, how much and where a specific gene is expressed.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. Regulatory sequences herein also refer to any of the group comprising a promoter, enhancer, silencer, intron sequence, 3'UTR and/or 5'UTR region, protein and/or RNA stabilizing elements.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule or derivative, which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits. In the context of the present invention, the promoter preferably is a plant-expressible promoter sequence. Promoters, however, that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. The terms "plant-operable" and "operable in a plant" when used herein, in respect of a promoter sequence, shall be taken to be equivalent to a plant-expressible promoter sequence.

In the present context, a "regulated promoter" or "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor. Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (AC, Ds, Spm, En, or other transposon). Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts. Conversely, a "strong promoter" drives expression of a coding sequence at high level, or at about $1/10$ transcripts to about $1/100$ transcripts to about $1/1,000$ transcripts.

The term "cell-specific" shall be taken to indicate that expression is predominantly in a particular cell or cell-type, preferably of plant origin, albeit not necessarily exclusively in said cell or cell-type.

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ. "Root-specific" means that the promoter is expressed in the root only and not in other tissues of the plant.

By "root-preferred" it is intended that expression of the heterologous nucleotide sequence is most abundant in root, but could also have low expression levels elsewhere in the plant. While some level of expression of the heterologous nucleotide sequence occurs in other plant tissue types, expression occurs most abundantly in the root including primary, lateral and adventitious roots.

By "root" is intended any part of the root structure, comprising the root cap, apical meristem, protoderm, ground meristem, procambium, endodermis, cortex, vascular cortex, epidermis, and the like.

The term "cell cycle specific" shall be taken to indicate that expression is predominantly cyclic and occurring in one or more, not necessarily consecutive phases of the cell cycle albeit not necessarily exclusively in cycling cells, preferably of plant origin.

Placing a nucleic acid molecule under the regulatory control of a promoter sequence, or in operable connection with a promoter sequence means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

"Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Examples of promoters suitable for use in gene constructs of the present invention include those listed in Table 4, amongst others. The promoters listed in Table 4 are provided for the purposes of exemplification only and the present invention is not to be limited by the list provided therein.

In the case of constitutive promoters or promoters that induce expression throughout the entire plant, it is preferred that such sequences are modified by the addition of nucleotide sequences derived from one or more of the tissue-specific promoters listed in Table 4, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al. 1987). Another example describes conferring root specific or root abundant gene expression by fusing the CaMV35S promoter to elements of the maize glycine-rich protein GRP3 gene (Feix and Wulff 2000—WO0015662). Such modifications can be achieved by routine experimentation by those skilled in the art.

The term "terminator" refers to a DNA sequence at the end of a transcriptional unit which signal termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Those skilled in the art will readily be in a position to provide additional promoters and terminators that are useful in performing the present invention.

TABLE 4

Exemplary plant-expressible promoters for use in the performance of the present invention

I: CELL-SPECIFIC, TISSUE-SPECIFIC, AND ORGAN-SPECIFIC PROMOTERS

| GENE SOURCE | EXPRESSION PATTERN | REFERENCE |
| --- | --- | --- |
| α-amylase (Amy32b) | aleurone | Lanahan et al, Plant Cell 4: 203-211, 1992; Skriver et al, Proc Natl Acad Sci USA 88: 7266-7270, 1991 |
| cathepsin β-like gene | aleurone | Cejudo et al, Plant Mol Biol 20: 849-856, 1992 |
| *Agrobacterium rhizogenes* rolB | cambium | Nilsson et al, Physiol Plant 100: 456-462, 1997 |
| AtPRP4 | flowers | salus.medium.edu/mmg/tierney/html |
| chalcone synthase (chsA) | flowers | Van der Meer et al, Plant Mol Biol 15: 95-109, 1990 |
| LAT52 | anther | Twell et al, Mol Gen Genet 217: 240-245, 1989 |
| apetala-3 | flowers | |
| chitinase | fruit (berries, grapes, etc) | Thomas et al, CSIRO Plant Industry, Urrbrae, South Australia, Australia; winetitles.com.au/gwrdc/csh95-1.html |
| rbcs-3A | green tissue (eg leaf) | Lam et al, Plant Cell 2: 857-866, 1990; Tucker et al., Plant Physiol 113: 1303-1308, 1992 |

TABLE 4-continued

Exemplary plant-expressible promoters for use
in the performance of the present invention

| | | |
|---|---|---|
| leaf-specific genes | leaf | Baszczynski et al, Nucl Acid Res 16: 4732, 1988 |
| AtPRP4 | leaf | salus.medium.edu/mmg/tierney/html |
| *chlorella* virus adenine methyltransferase gene promoter | leaf | Mitra and Higgins, Plant Mol Biol 26: 85-93, 1994 |
| aldP gene promoter from rice | leaf | Kagaya et al, Mol Gen Genet 248: 668-674, 1995 |
| rbcs promoter from rice or tomato | leaf | Kyozuka et al, Plant Physiol 102: 991-1000, 1993 |
| *Pinus* cab-6 | leaf | Yamamoto et al, Plant Cell Physiol 35: 773-778, 1994 |
| rubisco promoter | leaf | |
| cab (chlorophyll a/b/binding protein | leaf | |
| pea Blec4 gene | vegetative and floral epidermal tissues | Mandaci and Dobres, Plant Mol Biol 34: 961-965 |
| SAM22 | senescent leaf | Crowell et al, Plant Mol Biol 18: 459-466, 1992 |
| ltp gene (lipid transfer gene) | | Fleming et al, Plant J 2: 855-862, 1992 |
| *R. japonicum* nif gene | nodule | U.S. Pat. No. 4 803165 |
| *B. japonicum* nifH gene | nodule | U.S. Pat. No. 5008194 |
| GmENOD40 | nodule | Yang et al, Plant J 3: 573-585, 1993 |
| PEP carboxylase (PEPC) | nodule | Pathirana et al, Plant Mol Biol 20: 437-450, 1992 |
| leghaemoglobin (Lb) | nodule | Gordon et al, J Exp Bot 44: 1453-1465, 1993 |
| *Tungro bacilliform* virus gene | phloem | Bhattacharyya-Pakrasi et al, Plant J 4: 71-79, 1992 |
| pollen-specific genes | pollen; microspore | Albani et al, Plant Mol Biol 15: 605, 1990; Albani et al, Plant Mol Biol 16: 501, 1991 |
| Zm13 | pollen | Guerrero et al, Mol Gen Genet 224: 161-168, 1993 |
| apg gene | microspore | Twell et al, Sex Plant Reprod 6: 217-224, 1993 |
| maize pollen-specific gene | pollen | Hamilton et al, Plant Mol Biol 18: 211-218, 1992 |
| sunflower pollen-expressed gene | pollen | Baltz et al, Plant J 2: 713-721, 1992 |
| *B. napus* pollen-specific gene | pollen; anther; tapetum | Arnoldo et al, J Cell Biochem, Abstract No. Y101, 204, 1992 |
| root-expressible genes | roots | Tingey et al, EMBO J 6: 1, 1987 |
| tobacco auxin-inducible gene | root tip | Van der Zaal et al, Plant Mol Biol 16: 983, 1991 |
| β-tubulin | root | Oppenheimer et al, Gene 63: 87, 1988 |
| tobacco root-specific genes | root | Conkling et al, Plant Physiol 93: 1203, 1990 |
| *B. napus* G1-3b gene | root | U.S. Pat. No. 5401836 |
| SbPRP1 | roots | Suzuki et al, Plant Mol Biol 21: 109-119, 1993 |
| AtPRP1; AtPRP3 | roots; root hairs | salus.medium.edu/mmg/tierney/html |
| RD2 gene | root cortex | 2.cnsu.edu/ncsu/research |
| TobRB7 gene | root vasculature | 2.cnsu.edu/ncsu/research |
| AtPRP4 | leaves; flowers; lateral root primordia | salus.medium.edu/mmg/tierney/html |
| seed-specific genes | seed | Simon et al, Plant Mol Biol 5: 191, 1985; Scofield et al, J Biol Chem 262: 12202, 1987; Baszczynski et al, Plant Mol Biol 14: 633, 1990 |
| Brazil Nut albumin | seed | Pearson et al, Plant Mol Biol 18: 235-245, 1992 |
| legumin | seed | Ellis et al, Plant Mol Biol 10: 203-214, 1988 |
| glutelin (rice) | seed | Takaiwa et al, Mol Gen Genet 208: 15-22, 1986; Takaiwa et al, FEBS Lett 221: 43-47, 1987 |
| zein | seed | Matzke et al, Plant Mol Biol 14: 323-32 1990 |
| napA | seed | Stalberg et al, Planta 199: 515-519, 1996 |
| wheat LMW and HMW glutenin-1 | endosperm | Mol Gen Genet 216: 81-90, 1989; Nucl Acids Res 17: 461-462, 1989 |
| wheat SPA | seed | Albani et al, Plant Cell 9: 171-184, 1997 |

TABLE 4-continued

Exemplary plant-expressible promoters for use
in the performance of the present invention

| | | |
|---|---|---|
| cZ19B1, maize 19 kDa zein | seed | WO0011177 |
| mi1ps, maize myoinositol-1-Pi synthase | seed | WO0011177 |
| wheat α, β, γ-gliadins | endosperm | EMBO J 3: 1409-1415, 1984 |
| barley ltr1 promoter | endosperm | |
| barley B1, C, D, hordein | endosperm | Theor Appl Gen 98: 1253-1262, 1999; Plant J 4: 343-355, 1993; Mol Gen Genet 250: 750-60, 1996 |
| barley DOF | endosperm | Mena et al, Plant J 116: 53-62, 1998 |
| blz2 | endosperm | EP99106056.7 |
| synthetic promoter | endosperm | Vicente-Carbajosa et al, Plant J 13: 629-640, 1998 |
| rice prolamin NRP33 | endosperm | Wu et al, Plant Cell Physiol 39: 885-889, 1998 |
| rice α-globulin Glb-1 | endosperm | Wu et al, Plant Cell Physiol 39: 885-889, 1998 |
| maize END genes | endosperm | WO0012733 |
| barley END1 | endosperm | WO9808961 |
| barley NUC1 | nucellus | WO9808961 |
| rice OSH1 | embryo | Sato et al, Proc Natl Acad Sci USA 93: 8117-8122, 1996 |
| rice α-globulin REB/OHP-1 | endosperm | Nakase et al, Plant Mol Biol 33: 513-522, 1997 |
| rice ADP-glucose PP | endosperm | Trans Res 6: 157-168, 1997 |
| maize ESR gene family | endosperm | Plant J 12: 235-246, 1997 |
| *sorgum* γ-kafirin | endosperm | Plant Mol Biol 32: 1029-1035, 1996 |
| KNOX | embryo | Postma-Haarsma et al, Plant Mol Biol 39: 257-271, 1999 |
| rice oleosin | embryo and aleuron | Wu et al, J Biochem 123: 386, 1998 |
| sunflower oleosin | seed (embryo and dry seed) | Cummins et al, Plant Mol Biol 19: 873-876, 1992 |
| LEAFY | shoot meristem | Weigel et al, Cell 69: 843-859, 1992 |
| *Arabidopsis thaliana* knat1 | shoot meristem | Accession number AJ131822 |
| | shoot meristem | Accession number Z71981 |
| CLAVATA1 | shoot meristem | Accession number AF049870 |
| stigma-specific genes | stigma | Nasrallah et al, Proc Natl Acad Sci USA 85: 5551, 1988; Trick et al, Plant Mol Biol 15: 203, 1990 |
| class I patatin gene | tuber | Liu et al, Plant Mol Biol 153: 386-395, 1991 |
| PCNA rice | meristem | Kosugi et al, Nucl Acids Res 19: 1571-1576, 1991; Kosugi and Ohashi, Plant Cell 9: 1607-1619, 1997 |
| Pea TubA1 tubulin | Dividing cells | Stotz and Long, Plant Mol Biol 41: 601-614, 1999 |
| *Arabidopsis* cdc2a | cycling cells | Chung and Parish, FEBS Lett 362: 215-219, 1995 |
| *Arabidopsis* Rop1A | Anthers; mature pollen + pollen tubes | Li et al, Plant Physiol 118: 407-417, 1998 |
| *Arabidopsis* AtDMC1 | Meiosis-associated | Klimyuk and Jones, Plant J 11: 1-14, 1997 |
| Pea PS-IAA4/5 and PS-IAA6 | Auxin-inducible | Wong et al, Plant J 9: 587-599, 1996 |
| Pea farnesyltransferase | Meristematic tissues; phloem near growing tissues; light- and sugar-repressed | Zhou et al, Plant J 12: 921-930, 1997 |
| Tobacco (*N. sylvestris*) cyclin B1;1 | Dividing cells/ meristematic tissue | Trehin et al, Plant Mol.Biol. 35: 667-672, 1997 |
| *Catharanthus roseus* Mitotic cyclins CYS (A-type) and CYM (B-type) | Dividing cells/ meristematic tissue | Ito et al, Plant J 11: 983-992, 1997 |
| *Arabidopsis* cyc1At (=cyc B1;1) and cyc3aAt (A-type) | Dividing cells/ meristematic tissue | Shaul et al, Proc Natl Acad Sci USA 93: 4868-4872, 1996 |
| *Arabidopsis* tef1 promoter box | Dividing cells/ meristematic tissue | Regad et al, Mol Gen Genet 248: 703-711, 1995 |
| *Catharanthus roseus* cyc07 | Dividing cells/ meristematic tissue | Ito et al, Plant Mol Biol 24: 863-878, 1994 |

TABLE 4-continued

Exemplary plant-expressible promoters for use
in the performance of the present invention

II: EXEMPLARY CONSTITUTIVE PROMOTERS

| GENE SOURCE | EXPRESSION PATTERN | REFERENCE |
| --- | --- | --- |
| Actin | constitutive | McElroy et al, Plant Cell 2: 163-171, 1990 |
| CAMV 35S | constitutive | Odell et al, Nature 313: 810-812, 1985 |
| CaMV 19S | constitutive | Nilsson et al, Physiol Plant 100: 456-462, 1997 |
| GOS2 | constitutive | de Pater et al, Plant J 2: 837-844, 1992 |
| ubiquitin | constitutive | Christensen et al, Plant Mol Biol 18: 675-689, 1992 |
| rice cyclophilin | constitutive | Buchholz et al, Plant Mol Biol 25: 837-843, 1994 |
| maize histone H3 | constitutive | Lepetit et al, Mol Gen Genet 231: 276-285, 1992 |
| *alfalfa* histone H3 | constitutive | Wu et al, Nucleic Acids Res 17: 3057-3063, 1989; Wu et al, Plant Mol Biol 11: 641-649, 1988 |
| actin 2 | constitutive | An et al, Plant J 10: 107-121, 1996 |

III: EXEMPLARY STRESS-INDUCIBLE PROMOTERS

| NAME | STRESS | REFERENCE |
| --- | --- | --- |
| P5CS (delta(1)-pyrroline-5-carboxylate syntase) | salt, water | Zhang et al, Plant Sci 129: 81-89, 1997 |
| cor15a | cold | Hajela et al, Plant Physiol 93: 1246-1252, 1990 |
| cor15b | cold | Wlihelm et al, Plant Mol Biol 23: 1073-1077, 1993 |
| cor15a (−305 to +78 nt) | cold, drought | Baker et al, Plant Mol Biol 24: 01-713, 1994 |
| rd29 | salt, drought, cold | Kasuga et al, Nature Biotechnol 18: 287-291, 1999 |
| heat shock proteins, including artificial promoters containing the heat shock element (HSE) | heat | Barros et al, Plant Mol Biol 19 665-75, 1992. Marrs et al, Dev Genet14: 27-41, 1993. Schoffl et al, Mol Gen Genet 217: 246-53, 1989. |
| smHSP (small heat shock proteins) | heat | Waters et al, J Exp Bot 47: 325-338, 1996 |
| wcs120 | cold | Ouellete et al, FEBS Lett 423: 324-328, 1998 |
| ci7 | cold | Kirch et al, Plant Mol Biol 33: 897-909, 1997 |
| Adh | cold, drought, hypoxia | Dolferus et al, Plant Physiol 105: 1075-87, 1994 |
| pwsi18 | salt and drought | Joshee et al, Plant Cell Physiol 39: 64-72, 1998 |
| ci21A | cold | Schneider et al, Plant Physiol 113: 335-45, 1997 |
| Trg-31 | drought | Chaudhary et al, Plant Mol Biol 30: 1247-57, 1996 |
| osmotin | osmotic | Raghothama et al, Plant Mol Biol 23: 1117-28, 1993 |
| lapA | wounding, enviromental | WO99/03977 University of California/INRA |

IV: EXEMPLARY PATHOGEN-INDUCIBLE PROMOTERS

| NAME | PATHOGEN | REFERENCE |
| --- | --- | --- |
| RB7 | Root-knot nematodes (*Meloidogyne* spp.) | US5760386 - North Carolina State University; Opperman et al, Science 263: 221-23, 1994 |
| PR-1, 2, 3, 4, 5, 8, 11 | fungal, viral, bacterial | Ward et al, Plant Cell 3: 1085-1094, 1991; Reiss et al 1996; Lebel et al, Plant J 16: 223-233, 1998; Melchers et al, Plant J 5: 469-480, 1994; Lawton et al, Plant Mol Biol, 19: 735-743, 1992 |
| HMG2 | nematodes | WO9503690 - Virginia Tech Intellectual Properties Inc. |
| Abi3 | Cyst nematodes (*Heterodera* spp.) | unpublished |

TABLE 4-continued

Exemplary plant-expressible promoters for use
in the performance of the present invention

| | | |
|---|---|---|
| ARM1 | nematodes | Barthels et al, Plant Cell 9: 2119-2134, 1997 |
| | | WO 98/31822 - Plant Genetic Systems |
| Att0728 | nematodes | Barthels et al, Plant Cell 9: 2119-2134, 1997 |
| | | PCT/EP98/07761 |
| Att1712 | nematodes | Barthels et al, Plant Cell 9, 2119-2134, 1997 |
| | | PCT/EP98/07761 |
| Gst1 | Different types of pathogens | Strittmatter et al, Mol Plant-Microbe Interact 9: 68-73, 1996 |
| LEMMI | nematodes | WO 92/21757 - Plant Genetic Systems |
| CLE | geminivirus | PCT/EP99/03445 - CINESTAV |
| PDF1.2 | Fungal including *Alternaria brassicicola* and *Botrytis cinerea* | Manners et al, Plant Mol Biol, 38: 1071-1080, 1998 |
| Thi2.1 | Fungal - *Fusarium oxysporum* f sp. *matthiolae* | Vignutelli et al, Plant J 14: 285-295, 1998 |
| DB#226 | nematodes | Bird and Wilson, Mol Plant-Microbe Interact 7: 419-442, 1994 |
| | | WO 95.322888 |
| DB#280 | nematodes | Bird and Wilson, Mol Plant-Microbe Interact 7: 419-442, 1994 |
| | | WO 95.322888 |
| Cat2 | Nematodes | Niebel et al, Mol Plant-Microbe Interact 8: 371-378, 1995 |
| □Tub | Nematodes | Aristizabal et al (1996), 8$^{th}$ International Congress on Plant-Microbe Interaction, Knoxville US B-29 |
| sHSP | Nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | Nematodes | Fenoll et al (1997) In: Cellular and molecular aspects of plant-nematode interactions. Kluwer Academic, C. Fenoll, F. M. W. Grundler and S. A. Ohl (Eds.) |
| Hs1(pro1) | Nematodes | WO 98/122335 - Jung |
| nsLTP | viral, fungal, bacterial | Molina and Garcia-Olmedo FEBS Lett, 316: 119-122, 1993 |
| RIP | viral, fungal | Turner et al, Proc Natl Acad Sci USA 94: 3866-3871, 1997 |

In the context of the current invention, "ectopic expression" or "ectopic overexpression" of a gene or a protein are conferring to expression patterns and/or expression levels of said gene or protein normally not occurring under natural conditions. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect.

"Ectopic expression" not only can result in overexpression of a gene but can also result in "downregulation of expression", for instance of the homologous gene in the plant where expression if effected.

With "ectopic co-expression" is meant the ectopic expression or ectopic overexpression of two or more genes or proteins. The same or, more preferably, different promoters are used to confer expression of said genes or proteins.

Preferably, the promoter sequence used in the context of the present invention is operably linked to a coding sequence or open reading frame (ORF) encoding one of the inventive sugar beet polypeptides or a homologue, derivative and/or an immunologically active fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe 1998 (WO9836083), Lowe et al. 1989 (WO9853083), Lederer et al. 1999 (WO9915682) or Wang et al. 1999 (WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes, e.g. as described in Atkins et al. 1994 (WO9400012), Lenee et al. 1995 (WO9503404), Lutziger et al. 2000 (WO0000619), Prinsen et al. 1997 (WO9713865) and Scott et al. 1997 (WO9738116).

Modulating, including lowering, the level of active gene products or of gene product activity can be achieved by administering or exposing cells, tissues, organs or organisms to said gene product, a homologue, analogue, derivative and/ or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an inhibitor or activator of said gene product or the activity thereof. Such inhibitors or activators include proteins (comprising e.g. proteinases and kinases) and chemical compounds identified according to the current invention as described supra. In the context of the invention the term "agonist" refers to a substance that can be either a protagonist or an antagonist, i.e. can have either positive or negative effects, can be an enhancer or an inhibitor or a modulator as well.

In the context of the current invention is envisaged the downregulation of the expression the inventive sugar beet genes as defined higher. The invention further comprises downregulation of levels of the activity of the inventive sugar beet polypeptides whereby the inventive sugar beet polypeptides have been defined supra.

By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefore, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, colour, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (eg. anoxia, hypoxia, high temperature, low temperature, dehydration, light, daylength, flooding, salt, heavy metals, amongst others), including adaptive responses of plants to said externally-applied factors. "Stress" or "environmental stress" is a circumstance caused by elements present in the environment which may include but are not limited to drought, salt, dehydration, heat, cold, freezing, water logging, wounding, mechanical stress, oxidative stress, ozone, high light heavy metals, nutrient deprivation, toxic chemicals, pathogen (including viruses, bacteria, fungi, insects and nematodes) and combinations of these.

"Osmotic stress" is any kind of stress which alters the osmotic potential in the cell. For example osmotic stress can be caused by drought or salt or frost.

"Non-environmental stress" is a circumstance caused by elements or factors from the organism (e.g. gene defect).

As used herein, "stress tolerance" refers to the capacity to grow and produce biomass during stress, the capacity to reinitiate growth and biomass production after stress, and the capacity to survive stress. The term "stress tolerance" also covers the capacity of the plant to undergo its developmental program during stress similarly to under non-stressed conditions, e.g. to switch from dormancy to germination and from vegetative to reproductive phase under stressed conditions similarly as under non-stressed conditions. Furthermore it is shown that genes protecting against osmotic stress (like trehalose) also protect against oxidative stress (Benaroudj et al. 2001). Therefore a person skilled in the art can assume that when an isolated gene confers salt tolerance to a host organism when transfected herein, it could also confer oxidative stress tolerance. Oxidative stress occurs in situations of cold stress combined with high light or in situations of ozone stress, in case of necrosis as a result of pathogen infection or wounding, in case of scenescence or by application of certain herbicides (like atrazine or paraquat). Since the function of many osmoprotectants is actually unknown and that mannitol for example also has been shown to function as a scavenger of oxygen radicals, it can be assumed that oxidative stress also occurs in case of osmotic stress.

Means for introducing recombinant DNA into plant tissue or cells include, but are not limited to, transformation using $CaCl_2$ and variations thereof, in particular the method described previously (Hanahan 1983), direct DNA uptake into protoplasts (Krens et al. 1982; Paszkowski et al. 1984), PEG-mediated uptake to protoplasts (Armstrong et al. 1990) microparticle bombardment, electroporation (Fromm et al. 1985), microinjection of DNA (Crossway et al. 1986; Fromm et al. 1985), microparticle bombardment of tissue explants or cells (Christou et al. 1988), vacuum-infiltration of tissue with nucleic acid, or in the case of plants, T-DNA-mediated transfer from *Agrobacterium* to the plant tissue as described essentially (An et al. 1985; Dodds 1985; Herrera-Estrella et al. 1983a; Herrera-Estrella et al. 1983b). Methods for transformation of monocotyledonous plants are well known in the art and include *Agrobacterium*-mediated transformation (Cheng et al. 1997—WO9748814; Hansen 1998—WO9854961, Hiei et al. 1994—WO9400977; Hiei et al. 1998—WO9817813; Rikiishi et al. 1999—WO9904618; Saito et al. 1995—WO9506722), microprojectile bombardment (Adams et al. 1999—U.S. Pat. No. 5,969,213; Bowen et al. 1998—U.S. Pat. No. 5,736,369; Chang et al. 1994—WO9413822; Lundquist et al. 1999—U.S. Pat. No. 5,874,265/U.S. Pat. No. 5,990,390; Vasil and Vasil 1995—U.S. Pat. No. 5,405,765; Walker et al. 1999—U.S. Pat. No. 5,955,362), DNA uptake (Eyal et al. 1993—WO9318168), microinjection of *Agrobacterium* cells (von Holt 1994—DE4309203) and sonication (Finer et al. 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including the 'flower dip' transformation method; (Bechtold & Pelletier 1998; Trieu et al. 2000)), protoplast fusion, or electroporation, amongst others. Most preferably said plant is produced by *Agrobacterium*-mediated transformation.

The "seedling" is the juvenile plant that arises from the mature embryo after seed germination.

With "differentiation of a cell" it is understood that the cell develops unique features to be engaged for a specific function. Mostly differentiation is irreversible.

*Agrobacterium*-mediated transformation or agrolisfic transformation of plants, yeast, moulds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterised and resides in the right border outer region and is called overdrive (Peralta et al. 1986; van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimised T-DNA vectors such that vector backbone integration in the genome of a eukaryotic cell is minimised or absent. With "optimised T-DNA vector" is meant a T-DNA vector designed either to decrease or abolish transfer of vector backbone sequences to the genome of a eukaryotic cell. Such T-DNA vectors are known to the one familiar with the art and include those described previously (Hanson et al. 1999, Stuiver et al. 1999—WO9901563).

The current invention clearly considers the inclusion of a DNA sequence of the present invention encoding a DRE-binding factor DBF1, homologue, derivative or immunologically active fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation.

With "binary transformation vector" is meant a T-DNA transformation vector comprising: a T-DNA region comprising at least one gene of interest and/or at least one selectable marker active in the eukaryotic cell to be transformed; and a vector backbone region comprising at least origins of replication active in *Escherichia coli* and *Agrobacterium* and markers for selection in *Escherichia coli* and *Agrobacterium*. Alternatively, replication of the binary transformation vector in *Agrobacterium* is dependent on the presence of a separate helper plasmid. The binary vector pGreen and the helper plasmid pSoup form an example of such a system as described in e.g. (Hellens et al. 2000) or as available on the internet site http://www.pgreen.ac.uk.

The T-DNA borders of a binary transformation vector can be derived from octopine-type or nopaline-type Ti plasmids or from both. The T-DNA of a binary vector is only transferred to a eukaryotic cell in conjunction with a helper plasmid. Also known in the art are multiple binary vector *Agrobacterium* strains for efficient co-transformation of plants (Bidney and Scelonge 2000—WO0018939).

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *Agrobacterium tumefaciens* strain A281 (Hiei et al. 1994—EP0604662, Hiei et al. 1995—EP0687730). Super-binary transformation vectors are used in conjunction with a helper plasmid.

With "co-integrate transformation vector" is meant a T-DNA vector at least comprising:
a T-DNA region comprising at least one gene of interest and/or at least one selectable marker active in plants; and
a vector backbone region comprising at least origins of replication active in *Escherichia coli* and *Agrobacterium*, and markers for selection in *Escherichia coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al. 1997), and luciferase gene, amongst others. With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen & Chilton 1996; Hansen et al. 1997, Hansen and Chilton 1997—WO9712046).

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore includes intervening DNA sequences as defined supra. "Plant cell" comprises any cell derived from any plant and existing in culture as a single cell, a group of cells or a callus. A plant cell may also be any cell in a developing or mature plant in culture or growing in nature.

"Plant" or "Plants" comprise all plant species which belong to the superfamily Viridiplantae. The present invention is applicable to any plant, in particular monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp., *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp., *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburusi alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidatai*, *Zantedeschia aethiopica*, *Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

"Cereal" comprises crop plants with edible grain for example plants belonging to the grass family that is cultivated for its nutritious grains such as oats, barley, rye, wheat, rice, and corn etc.

With "yeast two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel & Fields 1997). Alternatively, a mammalian two-hybrid system can be used which includes e.g. a chimeric green fluorescent protein encoding reporter gene (Shioda et al. 2000). Yet another alternative consists of a bacterial two-hybrid system using e.g. HIS as reporter gene (Joung et al. 2000).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to, while the maximum size is not critical. In some applications, the maximum size usually is not substantially greater than that required to provide the desired activity and/or function(s) of the original sequence. Typically, the truncated amino acid will range from about 5 to about 333 amino acids or nuin length. More typically, however, the sequence will be a maximum of about 333 amino acids in length, preferably a maximum of about 330 amino acids. It is usually desirable to select sequences of at least about 10, 12 or 15 amino acids, or 25, 50, 75, 100, 125, 150, 175, 200, 225, 250, 275 up to a maximum of about 300 or 325 amino acids. For instance, the truncated nucleic acid will correspond in length with the amino acid fragment it encodes.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cell cycle interacting proteins. The reaction mixture may be a cell free extract of may comprise a cell or tissue culture. Suitable set ups for the method of the invention are known to the person skilled in the art and are, for example, generally described previously (Alberts et al. 1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

The present invention is further described by reference to the following non-limiting figures and examples.

FIGURE LEGENDS

FIG. 1

Amino acids alignments of BvCKA2 with the catalytic subunit of other CK2. The accession number and sources of each of the CK2 are as follows: AtCKA2 (*Arabidopsis thaliana*, Acc. number Q08466, SEQ ID NO: 17), ZmCKA2 (*Zea mays*, Acc. number P28523, SEQ ID NO: 18), RnCKA1 (*Ratus norvergicus* Ac. number P19139, SEQ ID NO. 19), XlCKA2 (*Xenopus laevis*, Ac. number P28020, SEQ ID NO: 20), and ScCKA2 (*Saccharomyces cerevisiae* Ac. number P19454, SEQ ID NO: 21). The identical amino acids are shaded. The boxed regions indicate important conserved residues in CKII. These include the motif 71-DWG-73 forming the catalytic site, the essential 63K and the highly basic 69-KKKKIK-75 domain (SEQ ID NO:28).

FIG. 2

Southern blot analysis of BvCKA2 gene. Genomic DNA was digested with BamHI (B), HindIII (H) and EcoRI (E) and separated on a 0.8% agarose gel. The DNA was then transferred onto a nylon membrane and UV cross-linked. Hybridization was performed under high-stringency conditions (see example 8) using two radiolabeled probes: a fragment of 887 bp included in the coding region of BvCKA2 cDNA (left panel), and a fragment of 323 bp corresponding to the 3 untranslated region of BvCKA2 cDNA (right panel).

FIG. 3

BvCKA2 complements the yeast double mutant cka1 cka2. The casein kinase thermosensitive yeast strain YDH8 (cka1 cka2) was transformed with either plasmid pYPGE15-BvCKA2 (4,5,6,7) or the empty plasmid (1,2,3) and grown at the permissive temperature of 25° C. (left) or at the thermosensitive temperature of 37° C. (right)

FIG. 4

Increased tolerance to NaCl stress in yeast by overexpression of ScCKA2 and BvCKA2. The yeast mutant strain JM26 was transformed with either the empty plasmid (pYPGE15) or the plasmid containing inserts encoding for ScCKA2 or BvCKA2. Transformed cells were tested for salt tolerance as described in example 7. Plates contained SD medium with leucine, adenine and 150 mM NaCl when indicated.

FIG. 5

BvCKA2 gene expression is up-regulated by NaCl stress. Northern analysis was performed as described in example 8. RNA was isolated from 3 week old sugar beet leaves at 0, 3, 6, 8 and 24 hours after growing with (+) or without (−) 250 mM NaCl. The same RNA blot was hybridized with a 3' UTR fragment of BvCKA2 and with an a 3 tubulin probe (AtTUBA, Ac. number M17189) from *Arabidopsis* used as control of filter transfer. Control of gel loading was done with ethidium bromide staining and is shown by the 3.5 Kb band of rRNA.

FIG. 6

SEQ ID NO 1 to 5: DNA sequences of the nucleic acids of the invention, start and stop codons are underlined. SEQ ID NO 6 to 10: amino acid sequences of the polypeptides of the invention.

FIG. 7

In vitro evaluation of the tolerance to NaCl of transgenic *Arabidopsis* expressing clone 154 cDNA (BcCKA2)

Culture medium: MS, NaCl concentrations: 0, 100 and 125 mM NaCl, Variables studied: % of plants with true leaves (A) and % of plants with cotyledons (B), Number of repetitions of the experiment: 6-8, Number of plants per concentration: 150-200, Statistical analysis: ANOVA, Confidence level: 99%

FIG. 8

Picture of *Arabidopsis* seedlings grown on MS medium supplemented with 100 mM NaCl. The sedlings were not transformed or transformed with the empty vector pBI121 or transformed with the 145 cDNA encoding BvCKA2.

FIG. 9

Quantification of radioactive phenylalanin incorporation into proteins of plants transfected with BveIF-1A.

EXAMPLES

Example 1

Plant Material

Sugar beet seeds (*Beta vulgaris* var. DITA) were sown on pots containing a mixture of sand and vermiculite (1:1 w/w). The plants were grown under greenhouse conditions (8 hours at 20° C., 16 hours at 25° C. with supplementary lighting to stimulate a minimum of 12 hours photoperiod). They were periodically irrigated with a nutrient solution containing 2.4 g/l Ca $(NO_3)_2.4H_2O$, 1 g/l $KNO_3$, 1 g/l $MgSO_4.7H_2O$, 0.3 g/l $KH_2PO_4$, 5.6 mg/l Fe-quelate (Kelantren, Bayer), 1.1 mg/l $ZnSO_4.7H_2O$, 3.3 mg/l $MnO_4.H_2O$, 0.3 mg/l $CuSO_4.5H_2O$, 3.8 mg/l $H_3BO_3$, 0.18 mg/l $(NH_4)_6Mo_7.4H_2O$. For the construction of the cDNA library, three week old plants were irrigated with 200 mM NaCl for 24 hours before harvesting. For the Northern blot analysis plants were irrigated with 250 mM NaCl and the leaves were harvested at different times as indicated in the legend to FIG. 5. Controls were treated in the same manner but $H_2O$ was supplied to the cultures instead of the NaCl solution.

Example 2

Yeast Strains and Culture Conditions

The *Saccharomyces cerevisiae* strain JM26 (MATa leu 2-3, 112 ura 3-1 trp1-1, ade 2-1 h is 3-11,15 can 1-100, ena 1-4::HIS3, nha1::TRP1) provided by J. M. Mulet (Universidad Politécnica de Valencia, Instituto de Biologia Molecularly Cellular de Plantas) was used for the screening of the sugar beet cDNA library and characterization of the CKA2 cDNA clone. Strain JM26 is a derivative of W303.1A (Wallis et al. 1989) with null mutations of the genes ENA1-4 and NHA1, encoding a $Na^+$-pumping ATPase and a $Na^+/H^+$ antiporter, respectively, responsible for most of the yeast sodium extrusion (Garciadeblas et al. 1993, Bañuelos et al. 1998). The CK2 temperature sensitive mutant strain YDH8 (MATa cka1-Δ1::HIS 3 cka2-Δ1::TRP1 ade2-101$^{ochre}$ his3-Δ200 leu2-Δ1 lys2-801$^{amber}$ trp1-Δ1 ura 3-52 [pDH8: LEU2 cka2-8]) was a kind gift of Dr. C. V. C. Glover, University of Georgia (Hanna et al. 1995).

Yeast were grown in either minimal synthetic glucose medium (SD) or rich medium (YPD). SD medium contained 2% glucose, 0.7% yeast nitrogen base without amino acids and 50 mM succinic acid, adjusted to pH 5 with Tris, plus the required amino acids [100 µg/ml leucine, 30 µg/ml adenine, 100 µg/ml methionine] as indicated. YPD medium contained 1% yeast extract, 2% Bacto peptone and 2% glucose. Media were supplemented with NaCl as indicated. Solid media contained 2% bacteriological-grade agar.

Example 3

Construction of a Sugar Beet cDNA Library Induced by Salt Stress

Directional cDNAs were synthesized (cDNA synthesis kit, Stratagene) using poly(A)$^+$ RNA prepared from leaves of salt-treated sugar beet plants. cDNAs were ligated into phage λPG15 vector and packaged using a Gigapack III gold packaging extract (Stratagene). This phage has inserted the excisable expression plasmid pYPGE15 (URA3 as a selection marker) that is usable directly for both *Escherichia coli* and yeast complementation (Brunelli and Pall, 1993). A plasmid cDNA library was recovered from λPG15 by the cre-lox recombinase system (Brunelli and Pall, 1993).

Example 4

Screening and Isolation of cDNA Clones Conferring Salt Tolerance to Yeast

To screen for sugar beet cDNAs which increase salt tolerance in yeast, the cDNA library constructed in pYPGE15 was used to transform the yeast mutant strain JM26 by the LiCl method (Gietz et al. 1992). Transformants selected on SD plates with leucine and adenine by uracil prototrophy were pooled and replated on screening medium (SD with leucine, adenine and methionine supplemented with 0.15 M NaCl) at a density of $2\times10^5$ cells per plate (12×12 cm). Methionine was added to the selective medium to avoid selection of the HAL2-like homologues already found in *Arabidopsis* (Quintero et al. 1996, Gil-Mascarell et al. 1999). Alternatively, for the selection of Li$^+$ resistant yeast cells, the transformants were replated on screening medium (SD with leucine and adenin supplemented with 20 mM LiCl). The putative positive clones were rescreened on the same NaCl or LiCl medium.

One of the confirmed NaCl tolerant clones, clone 154, was selected for further characterization. Plasmid DNA was isolated from the 154 yeast cells (pYPGE15+154) and reintroduced into JM26 to confirm that it conferred salt tolerance. Selection against the URA3-marked plasmid using fluorotic acid restored the salt sensitivity of the yeast cells. The insert of pYPGE15+154 was directly sequenced by the dye-primer cycle sequencing method using a DNA sequencer (Model ABI 377, PE Biosystems). After identifying the insert as subunit alpha of CK2 (see below) it was renamed as pYPGE15+BvCKA2.

Example 5

Cloning of the Yeast CKA2 Gene

The *Saccharomyces cerevisiae* CKA2 gene was PCR-isolated from genomic DNA. The amplification was performed with Pwo DNA polymerase (Roche Molecular Biochemicals) and the primers were designed according to the sequence of the genomic clone (GenBank Accession number: M33759). The sequence of the primers (Eco RI-Xho I sites underlined) is the following:

```
Forward primer
                                               (SEQ ID NO 11)
5'-ATGGATTAGAATTCTCATAGAGTTGTAAGGTCTCAGGG-3'
and reverse primer
                                               (SEQ ID NO 12)
5'-CCTCAGTTCTCGAGTTTATAAATGGAAATCAGTGGTGG-3'.
```

The 1.1 kb PCR-amplified product was Eco RI-Xho I digested and directionally cloned into the yeast expression vector pYPGE15. This construct, named pYPGE15+Sc-CKA2, was used to transform the yeast strain JM26 (Gietz et al. 1992). Sequence analysis confirmed that the insert contained in the pYPGE15 plasmid was the yeast gene CKA2.

Example 6

Complementation Studies of the CKA2 Yeast Mutant

As casein kinase 2 catalytic subunit genes (CKA1 and CKA2) are essential for yeast viability, the ck2 mutant strain YDH8 (cka1 cka2) carries the centromeric plasmid pDH8 (LEU2 marker) coding for a temperature sensitive allele of the catalytic subunit (cka2-8). This construct allows cells to grow at 25° C. but not at the restrictive temperature of 37° C. (Hanna et al. 1995). Plasmid pYPGE15+BvCKA2 was introduced into the YDH8 strain by transformation. Afterwards, plasmid pDH8 was removed from YDH8 by growing cells in rich medium to allow plasmid loss and selecting for leucine auxotrophy. Growth of yeast cells at 25 and 37° C. was investigated.

Example 7

Salt Tolerance Tests and Measurements of Intracellular Ion Concentrations

Yeast cultures were pregrown in liquid SD medium with leucine and adenine. Aliquots of saturated cultures were diluted (1:10) and spotted with an 8×6 stainless steel replica plater (SIGMA St. Louis, Mo.) on plates containing the indicated concentrations of salts. For measurements of intracellular ion concentrations 10 ml of yeast culture grown to exponential phase in SD plus leucine, adenine, methionine and 75 mM NaCl (absorbance of 0.7 at 660 nm measured with Spectronic 20D: Milton Roy, Rochester N.Y.) were centrifuged, washed three times by resuspension in ice-cold 10 mM $MgCl_2$ and finally resuspended in 1 ml of 10 mM $MgCl_2$. Cell concentration was determined by the absorbance at 660 nm, and intracellular ions were extracted by addition of concentrated HCl to a 0.1 M final concentration. After removal of cell debris by centrifugation, $K^+$ and $Na^+$ concentrations in the supernatant were determined by atomic absorption spectrometer (Varian) in flame emission mode. Intracellular water was estimated as previously described (Gaxiola et al. 1992).

Example 8

Southern and Northern Blot Analyses

Genomic DNA was prepared from leaves of 3 week old sugar beet according to Rogers and Bendich (1994). Five μg of DNA were digested with appropriate restriction enzymes, electrophoresed in 0.8% agarose gel and blotted onto a nylon membrane filter (Hybond N+, Amersham Life Science). The membrane filter was hybridized with two different $^{32}$P-labeled DNA probes. One of them corresponded to a 887 bp PCR amplified fragment (forward primer, 5'-CGAAGCTCT-CACTGTTCAATGG-3' (SEQ ID NO 13) and reverse primer, 5'-GGATGTGCCATTG CTTCTTTTGC-3' (SEQ ID NO 14)) including in the coding region of BvCKA2 cDNA. A second more specific fragment of 323 bp (forward primer, 5'-CTCTCAAGTTAGAGCTGCAGA-3' (SEQ ID NO 15) and reverse primer, 5'-GCTATTAGCAAACTATAT-TAAGTG-3' (SEQ ID NO 16)) includes the 3' non-coding region of BvCKA2 cDNA. Hybridization and washes were carried out under high-stringency conditions (65° C.) according to Church and Gilbert (1984).

For Northern blot analysis total RNA was isolated from control or $Na^+$-treated sugar beet leaves as described by Davis et al. (1998). Thirty μg of total RNA were separated on a 1% agarose gel containing 2.2% formaldehyde and blotted onto a nylon membrane filter (Hybond N, Amersham Life Science). Hybridization was carried out with the 3'UTR specific probe of 323 bp described above for the Southern blotting. The filter was washed twice with SSC 4×, 0.1% SDS for 5 min and twice with SSC 0.4×, 0.1 SDS for 5 min at 65° C. The same filter was rehybridized with a 1.9 Eco RI fragment comprising the $\alpha_3$ tubullin gene of *Arabidopsis* (Ludwig et al. 1987). Hybridization and wash temperatures were reduced to 55° C. for this heterologous probe.

Example 9

Rice Transformation with the Sugar Beet Genes

Expression of sugar beet genes involved in salt tolerance in yeast in rice mediating stress tolerance in rice.

To investigate the stress tolerance activation of the sugar beet stress tolerance genes in monocots, the aforementioned genes (SEQ ID NO. 1-5), operably linked to a promoter, are each transformed to rice using the standard transformation procedures well known to the persons skilled in the art and outlined in the following paragraph. After several time periods ranging from 1 day to 1 or more weeks, the seedling is checked for the expression of the transformed gene. This is done by growing the seedlings in organogenesis medium, and checking the presence of the DNA or mRNA by PCR or reverse PCR. After the confirmation of gene expression the transformed rice plants are checked for the enhanced tolerance to stress situations including salt, drought and cold (see WO97/13843). This is done by growing the transformed rice plants in medium containing increased amounts of NaCl or LiCl. Also the increased resistance to cold or drought is tested by growing the transformed plants in suboptimal growing temperatures and suboptimal levels of humidity, respectively (WO97/13843).

*Agrobacterium*-Mediated Rice Transformation

The sugar beet genes of the present invention can be operably linked to a promoter an cloned into a vector. These vectors can be transformed to *Agrobacterium tumefaciens* strain LBA4404 or C58 by means of electoporation and subsequently transformed bacterial cells can be selected on a solid agar medium containing the appropriate antibiotics.

For demonstration of the expression of the genes of current invention in rice, 309 mature dry seeds of the rice japonica cultivars Nipponbare or Taipei are dehusked, sterilised and germinated on a medium containing 2,4-dichlorophenoxy-acetic acid (2,4-D). After incubation in the dark for four weeks, embryogenic, scutellum-derived calli are excised and propagated on the same medium. Selected embryogenic callus is then co-cultivated with *Agrobacterium*. Co-cultivated callus is grown on 2,4-D-containing medium for 4 to 5 weeks in the dark in the presence of a suitable concentration of the appropriate selective agent. During this period, rapidly growing resistant callus islands develop. After transfer of this material to a medium with a reduced concentration of 2,4-D and incubation in the light, the embryogenic potential is released and shoots develop in the next four to five weeks. Shoots are excised from the callus and incubated for one week on an auxin-containing medium from which they can be transferred to the soil. Hardened shoots are grown under high humidity and short days in a phytotron. Seeds can be harvested three to five months after transplanting. The method yields single locus transformants at a rate of over 50% (Chan et al. 1993, Hiei et al. 1994).

Example 10

Transformation of *Arabidopsis* with *Beta vulgaris* CKA2 Gene

The tolerance to NaCl of transgenic plants expressing 154cDNA (BvCKA2) was studied. *Arabidopsis thaliana* plants (Ecotype Columbia) were transformed either with the empty plasmid pBI121 (CLONTECH) or pBI121BvCKA2 expressing the sugar beet CK2 protein kinase alystic subdomain (SEQ ID No. 6). BvCKA2 cDNA was inserted between the BamHI and SacI sites of pBI121. The contructs were introduced into *Agrobacterium tumefaciens* C58Rif$^R$ Rif strain (Van Larebeke et al. 1974). This strain was used to transform *Arabidopsis* plants by the floral dipping method.

The effect of NaCl on plant survival was determined in vitro and in greenhouse experiments.

In Vitro Experiments.

Figure 7:
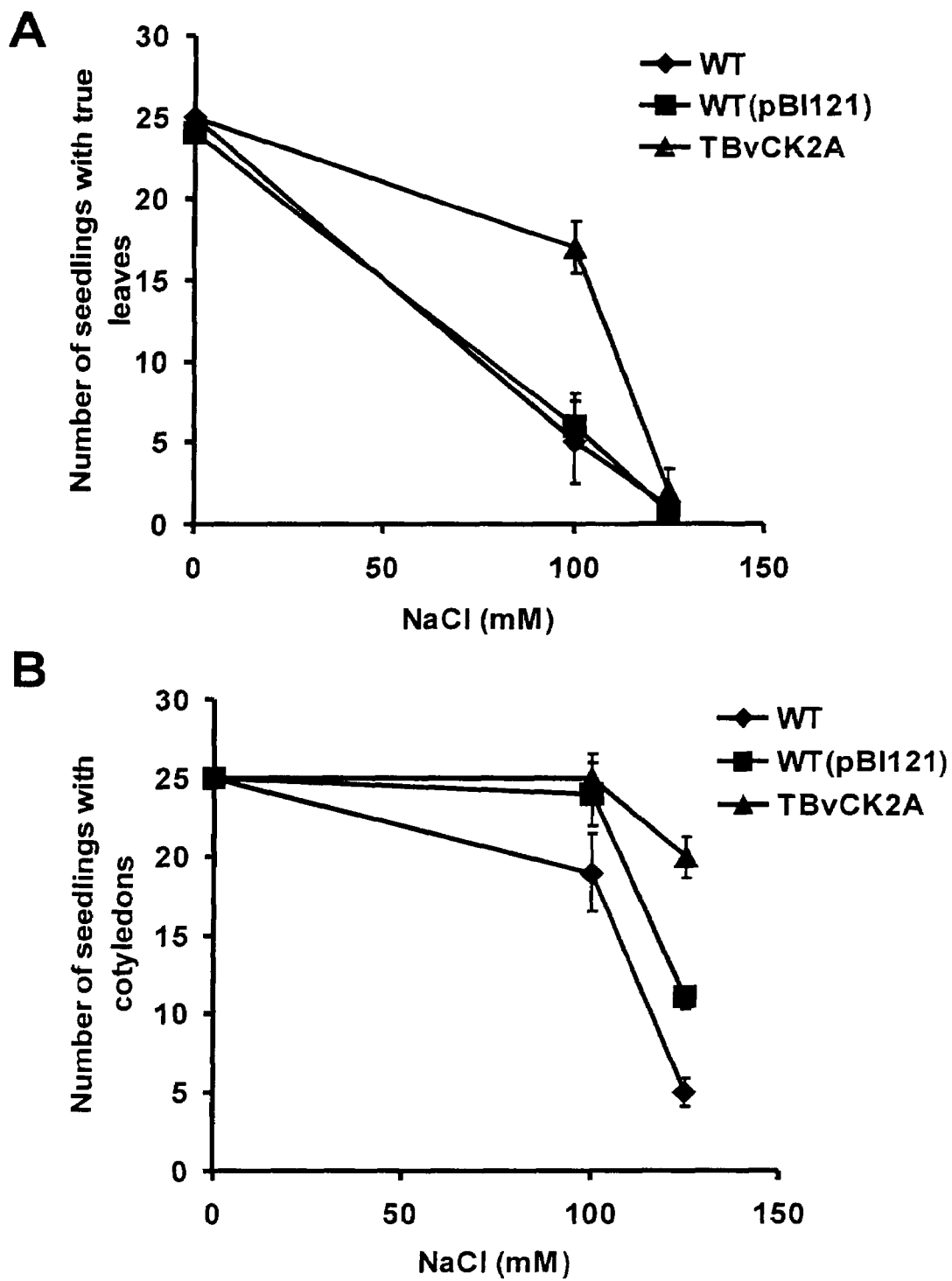
Figure 8:
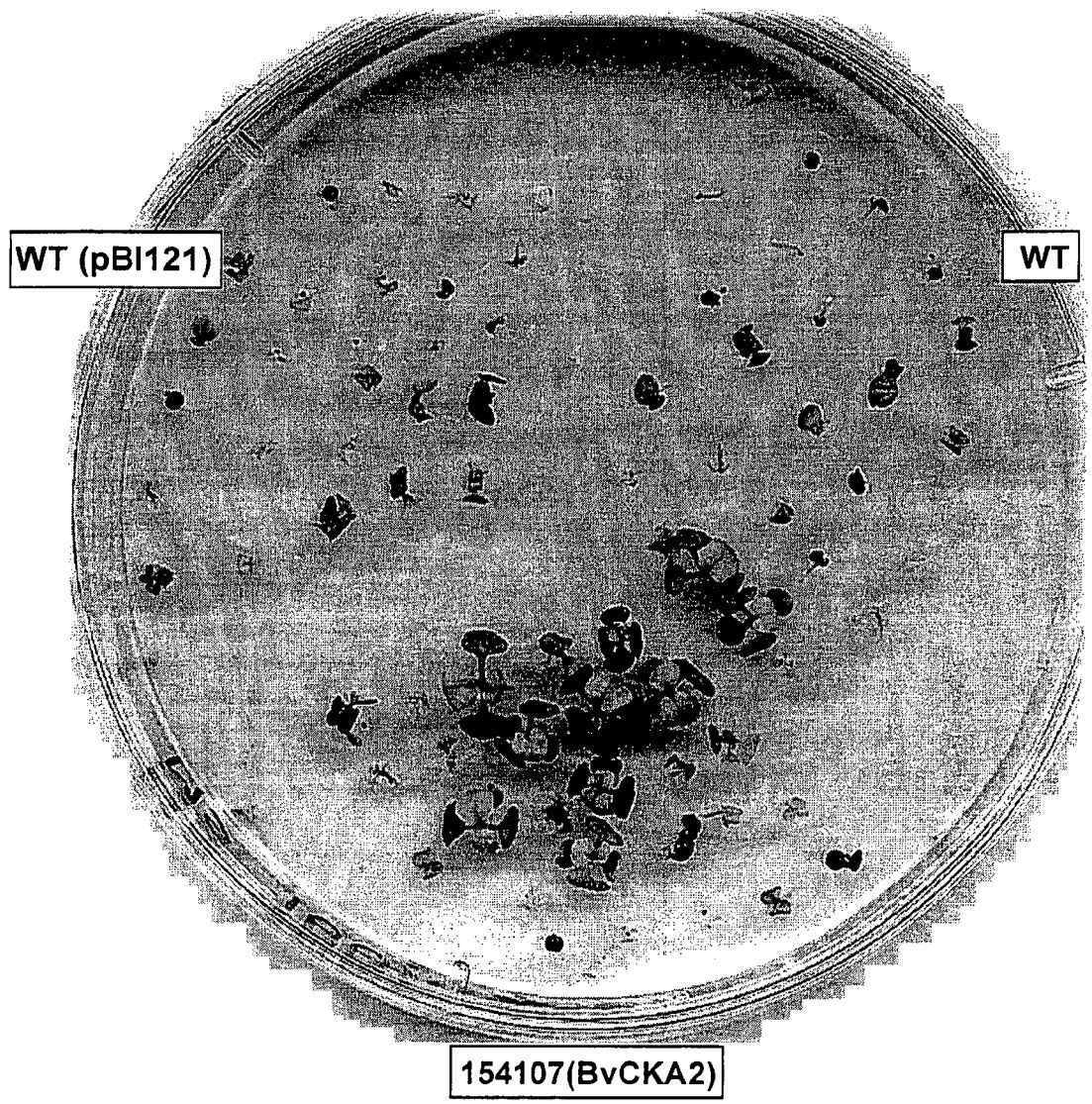

Seeds were grown in plates with MS medium plus 100 or 125 mM NaCl. Survival was determined as the number of seedlings that developed cotyledons and/or true leaves. Results are shown in FIGS. 7 and 8. These results clearly show that the *Arabidopsis* plants transfected with the cDNA having a nucleic acid sequence as represented in SEQ ID NO 1, encoding a the *Beta vulgaris* casein kinase α subunit having an amino acid sequence as represented in SEQ ID NO 6 of the present invention, clearly have an enhanced survival rate in salt stress conditions, when compared to wild type plants.

Greenhouse Experiments.

Plants were sown on pots containing a mixture of soil and vermiculite (2:1). The plants were grown as previously described (Kanhonou et al. 2001). Tolerance to 50 mM NaCl of control plants (Wild type plants and plants transformed with the empty plasmid) and plants overexpressing BvCKA2 was determined as the percentage of adult plants per sowed plants (Table 5). The dry weight was also determined (Table 5). The data are the mean ± SD.

TABLE 5

| PLANT | Control Medium | | 50 mM NaCl | |
|---|---|---|---|---|
| | % Adult plants/Sowed plants | Shoot dry weight (mg/plant) | % Adult plants/Sowed plants | Shoot dry weight (mg/plant) |
| Control WT | 93 ± 3 | 103 ± 8 | 46 ± 5 | 32 ± 7 |
| Transgenic Control | 89 ± 6 | 84 ± 27 | 48 ± 4 | 33 ± 10 |
| TBvCKA2,1 | 90 ± 3 | 96 ± 11 | 52 ± 1.5 | 33 ± 10 |
| TBvCKA2,2 | 93 ± 11 | 115 ± 11 | 58 ± 2 | 47 ± 3 |
| TBvCKA2,3 | 90 ± 6 | 110 ± 10 | 62 ± 4 | 45 ± 3 |

Example 11

The Use of BvCKA2 Gene for Controlling the Flowering Independently of the Photoperiod CK2 has recently been described as a Quantitative trait loci (QTL) involved in controlling flowering time (Takahashi et al. 2001). Specifically CK2 seems to be involved in controlling photoperiod sensitivity.

The inventors observed that the transgenic *Arabidopsis* plants as described in example 10 have a delay in the flowering time. This phenotype has a practical use, since growers are interested in controlling the process of flowering independently of the photoperiod. Delays or advances of flowering time is regulated by controlling the level of expression of CK2, or by modulating the activity of the CK2 protein in a plant cell or by using mutants of this protein.

Example 12

Functional Characterization of BveIF-1A

Figure 9:
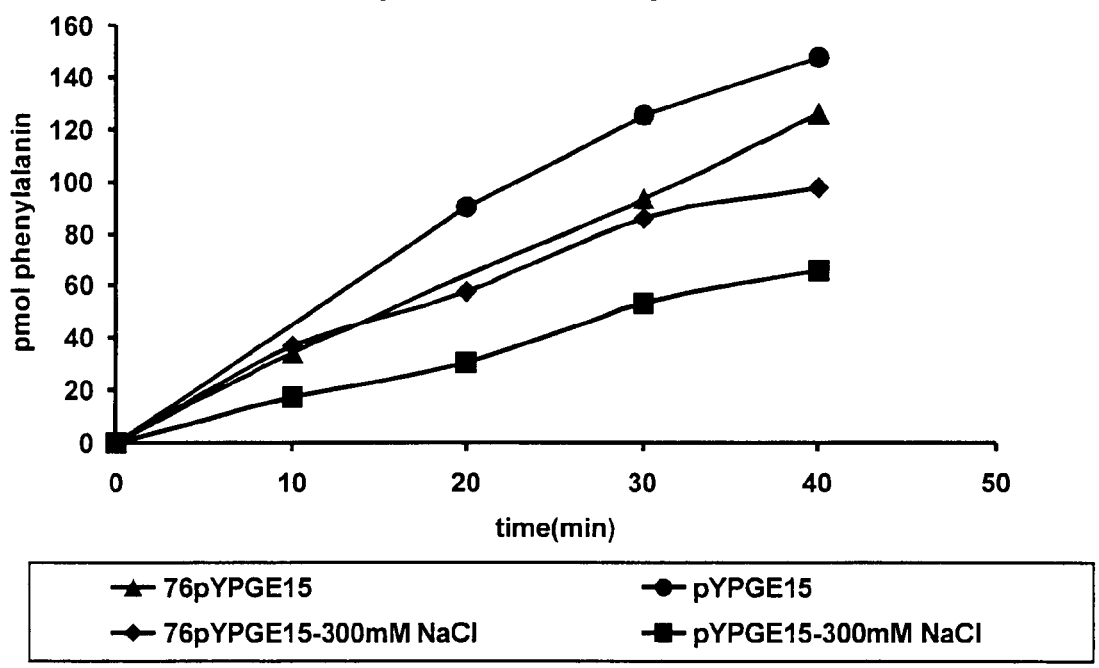

The *Saccharomyces cerevisiae* yeast strain JM26 (Kanhonou et al. 2001) was transformed with either the empty plasmid pYPGE15 (Brunelli and Pall 1993) or 76pYPGE15. Plasmid 76pYPGE15 carries a *Beta vulgaris* cDNA coding for the translation initiation factor e-IF1A. The incorporation of radioactive phenilalanine into yeast proteins was determined in liquid culture as described (Pascual Ahuir et al. 2001). The experiment was done in the presence (pYPGE15-300 mM NaCl, 76pYPGE15-300 mM NaCl) or absence (pYPGE15, 76pYPGE15) of 300 mM NaCl. Results are shown in FIG. 9. These results show clearly in the absence of NaCl the transgenic yeast carrying the BveIF-1A incorporate less phenylalanin compared to the cells transformed with the empty vector. On the contrary, when the yeast cells are put under severe salt stress conditions it is clear that protein synthesis occurs much better in the yeast cells transformed with the BveIF-1A.

REFERENCES

Alberts B., Bray D., Lewis J., Raff M., Roberts K., & Watson J. D. (1994) Molecular Biology of the Cell. Garland Publishing Inc.

Altschul et al. (1997) *Nucleic Acids Res.* 25, 3389-3402.

An G., Watson B. D., Stachel S., Gordon M. P., & Nester E. W. (1985) New cloning vehicles for transformation of higher plants. *EMBO J.* 4, 277-284.

Apse M. P. et al (1999) Salt tolerance conferred by overexpression of a vacuolar Na$^+$/H$^+$ antiport in *Arabidopsis*. *Science* 285, 1256-1258.

Armstrong C. L., Petersen W. P., Buchholz W. G., Bowen B. A., & Sulc S. L. (1990) Factors affecting PEG-mediated stable transformation of maize protoplasts. *Plant Cell Reports* 9, 335-339.

Bañuelos et al. (1998) *Microbiology* 144, 2749-2758.

Baron M. H. & Baltimore D. (1982) Antibodies against the chemically synthesized genome-linked protein of poliovirus react with native virus-specific proteins. *Cell* 28, 395-404.

Bartel P. L. & Fields S. (1997) The Yeast Two-Hybrid System. Oxford University Press.

Bechtold N. & Pelletier G. (1998) In planta *Agrobacterium*-mediated transformation of adult *Arabidopsis thaliana* plants by vacuum infiltration. *Methods Mol. Biol.* 82, 259-266.

Benaroudj et. al. (2001) Trehalose accumulation during cellular stress protects cells and cellular proteins from damage by oxygen redicals. *J. Biol. Chem.* 276(26), 924261-24267.

Bidwai et al. (1995) *J. Biol. Chem.* 270, 10395-10404.

Brunelli & Pall (1993) *Yeast* 9, 1309-1318.

Chan et al. (1993) *Plant Mol. Biol.* 22, 491-506.

Cho R. J., Mindrinos M., Richards D. R., Sapolsky R. J., Anderson M., Drenkard E., Dewdney J., Reuber T. L., Stammers M., Federspiel N., Theologis A., Yang W. H., Hubbell E., Au M., Chung E. Y., Lashkari D., Lemieux B., Dean C., Lipshutz R. J., Ausubel F. M., Davis R. W., & Oefner P. J. (1999) Genome-wide mapping with biallelic markers in *Arabidopsis thaliana*. *Nat. Genet.* 23, 203-207.

Church & Gilbert (1984) *Proc. Natl. Acad. Sci. USA* 81, 1991-1318.

Christou P., McCabe D. E., & Swain W. F. (1988) Stable transformation of soybean callus by DNA-coated gold particles. *Plant Physiol.* 87, 671-674.

Crossway A., Oakes J. V., Irvine J. M., Ward B., Knauf V. C., & Shewmaker C. K. (1986) Integration of foreign DNA following microinjection of tobacco mesophyllprotoplasts. *Mol. Gen. Genet.* 202, 179-185.

Davis et al. (1998) Basic methods in molecular biology. *Elsevier p* 143.

Dodds J. H. (1985) Plant genetic engineering. Cambridge University Press. Donald & Cashmore (1990) *EMBO J.* 9, 1717-1726.

Ellis J. G., Llewellyn D. J., Dennis E. S., & Peacock W. J. (1987) Maize Adh-1 promoter sequences control anaerobic regulation: addition of upstream promoter elements from constitutive genes is necessary for expression in tobacco. *EMBO J.* 6, 11-16.

Espunya et al. (1999) *Plant J.* 19, 655-666.

Fromm M., Taylor L. P., & Walbot V. (1985) Expression of genes transferred into monocot and dicot plant cells by electroporation. *Proc. Natl. Acad. Sci. U.S.A* 82, 5824-5828.

Garciadeblas et al. (1993) *Mol. Gen. Genet.* 236, 363-368.

Gaxiola R. et al. (1992) A novel and conserved salt-induced protein is an important determinant of salt tolerance in yeast. *EMBO J.* 11, 3157-3164.

Gietz et al. (1992) *Nucleic Acids Res.* 20, 1425.

Gil-Mascarell et al. (1999) *Plant J.* 17(4), 373-383.

Glover C. V. (1998) *Prog. Nucleic acid research* 59, 96-133.

Grein et al. (1999) *Mol. Cell. Biochem.* 191, 105-109.

Hanahan D. (1983) Studies on transformation of *Escherichia coli* with plasmids. *J. Mol. Biol.* 166, 557-580.

Hanks et al. (1995) *FASEB J.* 9, 576-596.

Hanna et al. (1995) *J. Biol. Chem.* 270(43), 25905-25914.

Hansen G. & Chilton M. D. (1996) "Agrolistic" transformation of plant cells: integration of T-strands generated in planta. *Proc. Natl. Acad. Sci. U.S.A* 93, 14978-14983.

Hansen G., Shillito R. D., & Chilton M. D. (1997) T-strand integration in maize protoplasts after codelivery of a T-DNA substrate and virulence genes. *Proc. Natl. Acad. Sci. U.S.A* 94, 11726-11730.

Hanson B., Engler D., Moy Y., Newman B., Ralston E., & Gutterson N. (1999) A simple method to enrich an *Agrobacterium*-transformed population for plants containing only T-DNA sequences. *Plant J.* 19, 727-734.

Harlow E. & Lane D. (1988) Antibodies: A Laboratory Manual. Cold Spring Harbor Laboratory Press.

Hasegawa, P. M. et al. (2000a). Plant cellular and molecular responses to high salinity. *Annu Rev. Plant Physiol. Plant Mol. Biol.* 51, 463-499.

Hasegawa et al. (2000b) *Trends Plant Sci.* 5(8), 317-9.

Haseloff J., Siemering K. R., Prasher D. C., & Hodge S. (1997) Removal of a cryptic intron and subcellular localization of green fluorescent protein are required to mark transgenic *Arabidopsis* plants brightly. *Proc. Natl. Acad. Sci. U.S.A* 94, 2122-2127.

Hellens R. P., Edwards E. A., Leyland N. R., Bean S., & Mullineaux P. M. (2000) pGreen: a versatile and flexible binary Ti vector for *Agrobacterium*-mediated plant transformation. *Plant Mol. Biol.* 42, 819-832.

Herrera-Estrella L., De Block M., Messens E. H. J. P., Van Montagu M., & Schell J. (1983a) Chimeric genes as dominant selectable markers in plant cells. *EMBO J.* 2, 987-995.

Herrera-Estrella L., Depicker A., Van Montagu M., & Schell J. (1983b) Expression of chimaeric genes transferred into plant cells using a Ti-plasmid-derived vector. *Nature* 303, 209-213.

Hiei Y., Ohta S., Komari T., & Kumashiro T. (1994) Efficient transformation of rice (*Oryza sativa* L.) mediated by *Agrobacterium* and sequence analysis of the boundaries of the T-DNA. *Plant J.* 6, 271-282.

Joung J. K., Ramm E. I., & Pabo C. O. (2000) A bacterial two-hybrid selection system for studying protein-DNA and protein-protein interactions. *Proc. Natl. Acad. Sci. U.S.A* 97, 7382-7387.

Kanhonou et al. (2001) *Plant Mol. Biol.* 47, 571-579.

Kenney, M. S. Ray, and T. C. Boles. Mutation typing using electrophoresis and gel-immobilized Acrydite probes. *Biotechniques* 25 (3): 516-521, 1998.

Krens F. A., Molendijk L., Wullems G. J., & Schilperoort R. A. (1982) In vitro transformation of plant protoplasts with Ti-plasmid DNA. *Nature* 296, 72-74.

Langemeier J. L., Cook R. F., Issel C. J., & Montelaro R. C. (1994) Application of cycle dideoxy fingerprinting to screening heterogeneous populations of the equine infectious anemia virus. *Biotechniques* 17, 484-6, 488, 490.

Lee et al. (1999) *Plant Physiol.* 119, 989-1000.

Lerner R. A. (1982) Tapping the immunological repertoire to produce antibodies of predetermined specificity. *Nature* 299, 593-596.

Lerner R. A., Green N., Alexander H., Liu F. T., Sutcliffe J. G., & Shinnick T. M. (1981) Chemically synthesized peptides predicted from the nucleotide sequence of the hepatitis B virus genome elicit antibodies reactive with the native envelope protein of Dane particles. *Proc. Natl. Acad. Sci. U.S.A* 78, 3403-3407.

Liddle J. E. & Cryer A. (1991) A Practical Guide to Monoclonal Antibodies. Wiley New York.

Li-Sucholeiki X. C., Khrapko K., Andre P. C., Marcelino L. A., Karger B. L., & Thilly W. G. (1999) Applications of constant denaturant capillary electrophoresis/high-fidelity polymerase chain reaction to human genetic analysis. *Electrophoresis* 20, 1224-1232.

Loffler J., Langui D., Probst A., & Huber G. (1994) Accumulation of a 50 kDa N-terminal fragment of beta-APP695 in Alzheimer's disease hippocampus and neocortex. *Neurochem. Int.* 24, 281-288.

Ludwig et al. (1987) *Proc. Natl. Acad. Sci. USA* 84, 5833-5837.

Magyar Z., Meszaros T., Miskolczi P., Deak M., Feher A., Brown S., Kondorosi E., Athanasiadis A., Pongor S., Bilgin M., Bako L., Koncz C., & Dudits D. (1997) Cell cycle phase specificity of putative cyclin-dependent kinase variants in synchronized alfalfa cells. *Plant Cell* 9, 223-235.

Marschner (1995) Mineral nutrition of higher plants. Springer, Berlin. Matthias K. et al. (1996) Salt stress induces an increased expression of V-type H+ATP-ase in mature sugar beet leaves. *Plant Mol. Biol.* 32(3), 543-547.

McCallum C. M., Comai L., Greene E. A., & Henikoff S. (2000a) Targeting induced local lesions IN genomes (TILLING) for plant functional genomics. *Plant Physiol* 123, 439-442.

McCallum C. M., Comai L., Greene E. A., & Henikoff S. (2000b) Targeted screening for induced mutations. *Nat. Biotechnol.* 18, 455-457.

Merrifield R. B. (1963) Solid phase peptide synthesis. I. The synthesis of a tetrapeptide. *J. Amer. Chem. Soc.* 85, 2149-2154.

Mizoguchi et al. (1995) *FEBS Lett.* 358, 199-204.

Murakami T., Simonds W. F., & Spiegel A. M. (1992) Site-specific antibodies directed against G protein beta and gamma subunits: effects on alpha and beta gamma subunit interaction. *Biochemistry* 31, 2905-2911.

Nadal et al. (1999a) *Eur. J. Biochem* 189, 251-257.

Nadal et al. (1999b) J. Bacteriol. 181, 6456-6462.

Niefind et al. (1998) *EMBO J.* 17, 2451-2462.

Padmanabha et al. (1990) *Mol. Cell. Biol.* 10, 4089-4099.

Palmgren G. (1997) Transgenic plants: environmentally safe factories of the future. *Trends Genet.* 13, 348.

Pascual Ahuir et al. (2001) *Mol. Cell. Biol.* 21, 16-25.

Paszkowski J., Shillito R. D., Saul M., Mandak V., & Hohn T. H. B. P. I. (1984) Direct gene transfer to plants. *EMBO J.* 3, 2717-2722.

Peralta E. G., Hellmiss R., & Ream W. (1986) Overdrive, a T-DNA transmission enhancer on the *A. tumefaciens* tumour-inducing plasmid. *EMBO J.* 5, 1137-1142.

Quintero et al. (1996) *Plant Cell* 8, 529-537.

Rogers and Bendich (1994) *Plant Mol. Biol.* Manual D1: 1-8.

Ross P., Hall L., & Haff L. A. (2000) Quantitative approach to single-nucleotide polymorphism analysis using MALDI-TOF mass spectrometry [In Process Citation]. *Biotechniques* 29, 620-629.

Russel B. L. (1998) Osmotic stress induces expression of choline monooxygenase in sugar beet and amaranth. *Plant Physiology* 116 (2), 859-865.

Sambrook J., Fritsch E. F., & Maniatis T. (1989) Molecular Cloning: A Laboratory Manual. Cold Spring Harbor Laboratory Press.

Semler B. L., Anderson C. W., Hanecak R., Dorner L. F., & Wimmer E. (1982) A membrane-associated precursor to poliovirus VPg identified by immunoprecipitation with antibodies directed against a synthetic heptapeptide. *Cell* 28, 405-412.

Serrano (1996) The isolation of genes which upon overexpression increase salt tolerance. *Int. Rev. Cytol.* 165, 1-52.

Shi H. et al. (2000) The *Arabidopsis thaliana* gene SOS1 encodes a putative $Na^+/H^+$ antiporter. *Proc. Natl Acad Sci USA* 97, 6896-68901.

Shioda T., Andriole S., Yahata T., & Isselbacher K. J. (2000) A green fluorescent protein-reporter mammalian two-hybrid system with extrachromosomal maintenance of a prey expression plasmid: Application to interaction screening. *Proc. Natl. Acad. Sci. U.S.A* 97, 5220-5224.

Sugano et al. (1998) *Pro. Nat. Acad. Sci. USA* 96, 12362-12366.

Suggano et al. (1999) *Pro. Nat. Acad. Sci. USA* 95, 11020-11025.

Syvanen A. C. From gels to chips: "minisequencing" primer extension for analysis of point mutations and single nucleotide polymorphisms. *Hum. Mutat.* 13 (1):1-10, 1999.

Tamura R. N., Cooper H. M., Collo G., & Quaranta V. (1991) Cell type-specific integrin variants with alternative alpha chain cytoplasmic domains. *Proc. Natl. Acad. Sci. U.S.A* 88, 10183-10187.

Tapp, I. L. Malmberg, E. Rennel, M. Wik, and A. C. Syvanen. Homogeneous scoring of single-nucleotide polymorphisms: comparison of the 5'-nuclease TaqMan assay and Molecular Beacon probes. *Biotechniques* 28 (4):732-738, 2000.

Takahashi et al. (2001) Hd6, a rice quantitative trait locus involved in photoperiod sensitivity, encodes the alpha subunit of protein kinase CK2. *Proc Natl Acad Sci USA* 98, 7922-7.

Teney & Glover (1999) *Mol. Cell. Biochem.* 191, 161-167.

Trieu A. T., Burleigh S. H., Kardailsky I. V., Maldonado-Mendoza I. E., Versaw W. K., Blaylock L. A., Shin H., Chiou T. J., Katagi H., Dewbre G. R., Weigel D., & Harrison M. J. (2000) Technical Advance: Transformation of *Medicago truncatula* via infiltration of seedlings or flowering plants with *Agrobacterium. Plant J.* 22, 531-541.

Van Haaren M. J., Sedee N. J., Schilperoort R. A., & Hooykaas P. J. (1987) Overdrive is a T-region transfer enhancer which stimulates T-strand production in *Agrobacterium tumefaciens. Nucleic Acids Res.* 15, 8983-8997.

Van Larebeke et al. (1974) *Nature* 252, 169-170.

Vidal-Puig A. & Moller D. E. (1994) Comparative sensitivity of alternative single-strand conformation polymorphism (SSCP) methods. *Biotechniques* 17, 490-2, 494, 496.

Wallis et al. (1989) *Cell* 58, 409-419.

Wang K., Genetello C., Van Montagu M., & Zambryski P. C. (1987) Sequence context of the T-DNA border repeat element determines its relative activity during T-DNA transfer to plant cells. *Mol. Gen. Genet.* 210, 338-346.

Woulfe J., Lafortune L., de Nadai F., Kitabgi P., & Beaudet A. (1994) Post-translational processing of the neurotensin/neuromedin N precursor in the central nervous system of the rat-II. Immunohistochemical localization of maturation products. *Neuroscience* 60, 167-181.

Yoon K., Cole-Strauss A., & Kmiec E. B. (1996) Targeted gene correction of episomal DNA in mammalian cells mediated by a chimeric RNA.DNA oligonucleotide. *Proc. Natl. Acad. Sci. USA* 93, 2071-2076.

Zhu J. K., (1997) Molecular aspects of osmotic stress in plants. *CRC Crit. Rev. Plant Sci.* 16, 253-277.

---

The invention claimed is:

1. A method for enhancing osmotic stress tolerance in a plant comprising introducing and expressing of a nucleic acid molecule encoding a protein having the amino acid sequence of SEQ ID NO:8 in cells, tissues or parts of said plant, wherein expression of said nucleic acid molecule results in an enhancement of osmotic stress tolerance in the plant relative to an untransformed plant having a similar genetic background.

2. A method for enhancing osmotic stress tolerance in a plant comprising introducing and expressing of a nucleic acid molecule having the sequence of SEQ ID NO:3, wherein expression of said nucleic acid molecule results in an enhancement of osmotic stress tolerance in the plant relative to an untransformed plant having a similar genetic background.

3. The method according to claim 1 or claim 2, wherein said expression of said nucleic acid molecule occurs under the control of a promoter.

4. The method according to claim 1 or claim 2, wherein said osmotic stress is caused by salt.

5. The method according to claim 1 or claim 2, wherein said osmotic stress is caused by drought.

6. The method according to claim 1 or claim 2, wherein said osmotic stress is caused by frost.

7. The method according to claim 1 or claim 2, wherein said osmotic stress is caused by cold.

8. An isolated nucleic acid molecule encoding a protein for enhancing osmotic stress tolerance to a plant, wherein said nucleic acid molecule is selected from the group consisting of: (a) a nucleic acid molecule comprising the DNA sequence as given in SEQ ID NO: 3; (b) a nucleic acid molecule comprising the RNA sequence corresponding to SEQ ID NO:3; and (c) a nucleic acid molecule encoding the protein of SEQ ID NO: 8.

9. A vector comprising the nucleic acid molecule according to claim 8.

10. The vector according to claim 9 which is an expression vector wherein said nucleic acid molecule is operably linked to one or more control sequences allowing the expression of said nucleic acid molecule in prokaryotic or eukaryotic host cells.

11. A host cell comprising the nucleic acid molecule according to claim 8.

12. The host cell according to claim 11, wherein the host cell is a bacterial, insect, fungal, yeast, plant or animal cell.

13. A method for increasing the expression of a polypeptide having the sequence of SEQ ID NO:8 comprising introducing and expressing the nucleic acid molecule of claim 8 operably linked to one or more control sequences, stably integrated into the genome of a plant cell, wherein said introducing and expressing of the nucleic acid molecule results in an increase in expression of the polypeptide in said plant cell relative to an untransformed plant cell having a similar genetic background.

14. A method for the production of a transgenic plant cell, plant tissue or plant comprising introducing the nucleic acid molecule of claim 8 in said plant cell, plant tissue or plant.

15. A method for enhancing osmotic stress tolerance in a plant cell, tissue or plant comprising introducing and expressing of the nucleic acid molecule as identified in any one of claims 8-10 into said plant cell, tissue or organ of said plant, wherein said introducing and expressing of the nucleic acid molecule results in an enhancement of osmotic stress tolerance in said plant cell, plant tissue or plant relative to an untransformed plant cell, plant tissue or plant having a similar genetic background.

16. The method according to claim 13 further comprising regenerating a plant from said plant cell.

17. A transgenic plant cell comprising the nucleic acid molecule of claim 8 which is operably linked to a promoter allowing transcription and/or expression of said nucleic acid molecule in said plant cell.

18. The transgenic plant cell of claim 17, wherein said nucleic acid molecule is stably integrated into the genome of said plant cell.

19. A transgenic plant or plant tissue comprising the plant cell of claim 17.

20. The transgenic plant of claim 19 which displays increased tolerance to osmotic stress compared to an untransformed plant having a similar genetic background.

21. A transgenic part of the plant of claim 19, wherein said transgenic part comprises said nucleic acid molecule.

22. The transgenic part of claim 21 which is selected from the group consisting of seeds, leaves, fruits, stem cultures, rhizomes and bulbs, wherein said transgenic part comprises said nucleic acid molecule.

23. Transgenic progeny obtained from the plant or plant tissue of claim 19 wherein said plant progeny comprises said nucleic acid molecule.

24. A diagnostic composition comprising the nucleic acid molecule of claim 8.

25. A diagnostic composition comprising the vector of any one of claims 9 and 10.

26. The method according to claim 14 further comprising regenerating a plant from said plant cell.

27. The method according to claim 15 further comprising regenerating a plant from said plant cell.

28. A transgenic plant produced by the method of claim 14.

29. A transgenic plant produced by the method of claim 16.

30. A transgenic part of the plant of claim 20 wherein said transgenic part comprises said nucleic acid molecule.

31. A transgenic plant or plant tissue comprising the plant cell of claim 18.

* * * * *

SEQUENCE LISTING

<160> NUMBER OF SEQ ID NOS: 28

<210> SEQ ID NO 1
<211> LENGTH: 1527
<212> TYPE: DNA
<213> ORGANISM: Beta vulgaris

<400> SEQUENCE: 1

-continued

```
gaattcggca cgaggaaatt tgagattgtc gggttcactc ctcttcacac tactaacttt      60
tttccatctt ctctctcact cgtcttactg tgcgcactcc ttgctctccg tgcaccggtg     120
gcgcatcctc ctatcctgcg cccatcaacc ctaaatttcg ccgccgctaa tttcgagatc     180
tccgccgacg caaattctcc gatgtcgaag tcgcgagttt acgccgacgt taatgttctc     240
cgacctcgag agtactggga ttacgaagct ctcactgttc aatggggtga tcaagatgac     300
tatgaagtcg tgcggaagat tggaaggggg aaatacagtg aagtttttga aggattaaac     360
gtcaatagta atgaacgatg cgttatcaag atcctgaaac ctgtgaagaa gaaaagatc     420 aaaagagaga taaaaatcct tcagaaccta tgtggggac caaacgtcat aaagctgctt     480
gatatcgtca gggatcagca ctccaaaaca ccaagcttag tttttgagtt tgtcaacagt     540
acagatttca aagttctgta tccaacgtta tctgattatg acatacgtta ttacatctat     600
gagcttctga aggccttaga tttctgccat tcacaaggga aatgcaccg agatgtcaag     660 cctcataatg taatgataga ccatgaattg aggaaactcc ggttaataga ttggggtctg     720
gcagagttct accatccagg gaaggaatac aatgttcgtg tggcttcgag atactttaag     780
gggccggaac ttcttgttga tttacaagac tatgactatt ccttggacat gtggagcctt     840
ggttgcatgt ttgctgggat gattttccgg aaagaaccat tcttctatgg tcatgacaac     900
catgatcagc ttgttaaaat tgctaaggta cttggaacag atgaactgaa tgcttatttg     960
aacaagtatc atttggagct tgatcctcaa cttgatgctc ttgttggaag gcacagcagg    1020
aagccatggt caagatttgt taatccggat aatcagcatt tagtttcccc tgaggctatt    1080
gactttcttg ataagcttct tcgctatgac caccaggata ggcttactgc aaaagaagca    1140
atggcacatc cttatttctc tcaagttaga gctgcagaga gtagcagaat gcggacacaa    1200
tagctcgtca ctctaataca tacttgagaa tgatgatttc cattgtagag tgtttcatgt    1260
taagtcattg actgtgttcc cgtcttaaac attgcagcta cttgcagcgt caggtagaca    1320
gctttgattg cgcggggaaa ttttatgtaa aatgcatgat tactagtctt tctaaaactg    1380
caaatctgca atgccacaaa ctattgtact gctattttaa ttgttgaagc cctctgtaca    1440
tctccaacat tggttgtcac ttaatatagt ttgctaatag catctgtaaa aaaaaaaaa    1500 aaaaaaaaaa aaaaaaaaa aaaaaaa                                        1527
```

<210> SEQ ID NO 2
<211> LENGTH: 1743
<212> TYPE: DNA
<213> ORGANISM: Beta vulgaris

<400> SEQUENCE: 2

```
aattcggcac gagcacagct ccactccctc tttctctcaa gaagacgaac acacaccaat     60
tcagatctga agtttcgtat tttctctctc ctcttcctcg acatcttcct cgtgctcgaa    120
ttgcaagcgt tccaggcatc aaatttgcct attcccgggt tgaaacaca taacggacta    180 aatatcaaag cagtaaagat ggaactgact cttacacgcc ctgatgactg gcatctacat    240
ctccgcgatg gagatcttct tgctgctgtt gctcctcaca gtgcaagaca ttttggaagg    300
gcaatcgtta tgccgaatct aaggcctcct gttactacta caggtgctgc tattgcttac    360
cgaaagtcta ttatggaagt attgcctgat gatagcgact tcaatcctct catgacactt    420
tatttgactg atacgaccag ccctaatgag atcaagcttg ccagaaaaag tgaggtggta    480
tatgctgtca aattataccc tgctggcgca acaactaatt tcaggacgg tgtcactgat    540 cttttaggaa agtgtctgcc tgtgcttgaa gagatggctg agcaagatat gcctcttctg    600
```

```
gtccatggag aagttacaga tcctgatgta gatatatttg atcgtgaaaa ggtttttatt      660
gagtcagttt taagaccttt aattcagaaa ttaccacagc taaaggttgt gatggaacac      720
atcactactg ctgatgctgt caagtttatt gagtcctgta atggaggaaa tgtagcagcc      780
actgtgacgc cgcagcacct tgttctgaat agaaactctc tcttccaagg agggttgcaa      840
ccgcataact attgtcttcc agtgctcaaa agagaaatcc atagacaggc acttgtttca      900
gcggtaacca gcgggagcaa gcaatatttt cttgggactg atagtgctcc tcatgaaagg      960
cggaggaaag aatgttcgtg tggatgtgct ggaatctata attccctgt tgctctatca      1020 ctatatgcca agtatttga agaggctggt gcccttgaca agttagaggc atttacaagc      1080
tttaatggac ccgatttcta tggtcttcca aggaatacgt cgaagatcaa gttgaaaaaa      1140
gaaccatgga aagtcctaga gcgtatacct ttcccatccg agaaataat ccctatgttt       1200 gctggacaaa tgcttgactg aagccatct ttctgagatc atctctcatc catctttacc       1260
atctgtactt tccctttctt tcaatgcatt tgtgtctcat tgatgagaaa tgtgtactgc      1320
ttgaacatca attttgtggg cactcagttt gtaagacctc ttaccttttt tagaaagaaa      1380
caaggaccaa caagtgcttg gatcaggtgg tagtaagagg tttcggctca atcaaaggat      1440
tcagattcga gcttcaagca cttgttcgga gagctccccc caatcgagcc ttccgcgccc      1500
gaatctacgg tcgttcgaac tctggtaggc tctaaattac tgggtgtttt tctttatctt      1560
ctcccccttt aaatgaaaaa aagggggcac agattataag ttccaattta atttctacaa      1620
gacaaattta taataattct aataaagttc tataccagct taatcttacc tttatttaa      1680 aaaaaaaaaa aaaaaaaaaa aaaaaaaaaa aaaaaaaaaa aaaaaaaaaa aaaaaaaaaa      1740
aaa                                                                    1743

<210> SEQ ID NO 3
<211> LENGTH: 634
<212> TYPE: DNA
<213> ORGANISM: Beta vulgaris

<400> SEQUENCE: 3
ctagcaaaca acaacaaact caaaaaccag cctttttttc acaaaatcag aaccgtctga       60
tctagggttt tctggtagag agaaaagatg ccgaagaaca aggaaaggg aggaaagaac       120 aggaagagag gaaagaatga agctgatgat gagaaaagag aacttgtttt caaagaagat      180
ggacaagagt acgcgcaagt tgttcgtatg ctcggtaatg gccgttgtga agctacttgc      240
atcgattatg ttaagcgtct ttgtcatatt cgtggtaaga tgcacaaaaa agtctggatc      300
gctgctggtg atattattct cgtcggtctt cgcgattatc aggatgacaa ggctgatgtg      360
atcctaaagt atatgccaga tgaagccagg ttgctcaaag cttacggcga gttgccagac      420
aacatcagac ttaatgaagg tgttgctaat ctcgatgagg aagacgatgg tggtgctgat      480
gactacatcg agttcgaaga cgaagacatt gataagatat aagcaattta gtttgtttta     540
caaatgcacc tttactgcga ctgttgaacc ttatatgtca attgtatgtt tcttgggttt      600
gatcaatatt tgatgtaaaa aaaaaaaaaa aaaa                                  634

<210> SEQ ID NO 4
<211> LENGTH: 845
<212> TYPE: DNA
<213> ORGANISM: Beta vulgaris

<400> SEQUENCE: 4
```

```
tgtcagtcac aatcatcaga ctatatcaat ggttcgtaag cgatttcaag acgtgcaaac      60
aggtattcaa tgggctaaag tgttgagaaa agtgggatta ggcaaggaag acaggtactt     120
ttggaagcaa gtgggtaagg cattgctatg cacctatgca gtgtttggtg cagcatgggt     180
ttacaatgaa acatcaccac ttgggtggtg gacattgaag cctcgtccta aggaggagaa     240
agaactagct catctttacg aacggcgaga gtttccgtat ccaggtgaca agaagcaat      300 ggaagagttt gtaaccaaag gtgggatgat tggtactacc attggcccga aggaacagt      360 tgaaactgat aaggattcat ttaactatca gaaagcattg caggataaga agtttgagca     420
ggaggctcat aagttgtggt ttaggatgag gaatgaagtg gttgcggagc ttcaagaaaa     480
gggtttcgat gtcgagtgat acgattagga atggcaatga caataacatc aagcctctag     540
gtgaagtatt tgttttgaac tggtttgtgt tagcttatta gctttgtgga ataatgcct      600 tggtttgtgg tgctttaagt ttaaggattg aacatatata ttgtttggga cttgagagtt     660
ccaagaaaag ggttttgatg tcagtgaaac aattgaggaa tggcaatgac aattacatca     720
agcctctata ggtgaagtat ggtctgaact aattctgtta gccttaagtt gtgtgcctta     780
aagtttaagg attgaacata tctataattg ggacttgaga atgggacaat aagatacaat     840
tgggg                                                                 845

<210> SEQ ID NO 5
<211> LENGTH: 879
<212> TYPE: DNA
<213> ORGANISM: Beta vulgaris

<400> SEQUENCE: 5
atgatgggtg aaggtaacag ggacaagagt aagaagaaga agaagaagag aggtggtgct      60
aaaagaagga tgactgttga acaaacttca gctttgaaat ctgtaaatga atgggtttat     120
ttggctcaac atgctgatga acaagagaag atcaaagagg atgattttct acctgaaatt     180
atgcgcattg ctagagtttc tgagaatatt gtgtttgaat tgcattctca tactatttgc     240
agtgatgggt ttttatcccc ttctgctctt gttgagaaag ctcatcaaaa tggggtgaaa     300
gttcttgctt tgactgatca tgacacaatg tctggtatcc ccgaggccct gcaagcggcc     360
ggtagatttg gtatcaagat tattccaggt gttgagatca gttcagtttt ctctactaca     420
agagatgaat ctgaagcaga agaaccagtt cacattcttg catattatag cagctgtgga     480
cctgcaagat ttgaagagtt agatcaatttt ttggccaaca taaggggacgg acgttacctt     540 cgtgccaaaa atatgctcgc aaaacttgcg aaactcaaaa agcccgtcaa gtgggaacgt     600
gtcataaaga ttgcaggcaa tggagttgct cctgggagac tgcatgtagc tcgtgctttg     660
ttggaagctg gccatgttga agatcttaaa caagcattcg atcggtatct tcatgatggg     720
ggccctgctt attccaaggg aagtgagcct tctgcggaag aagctgtgca aatggtgtgt     780
aaaactgggg gaatagctgt cttggcacat ccatgggcat taaaaaatcc ttccccagta     840
gtcaacagat tgaaaggagg caggtcttca tggaattga                            879

<210> SEQ ID NO 6
<211> LENGTH: 333
<212> TYPE: PRT
<213> ORGANISM: Beta vulgaris

<400> SEQUENCE: 6

Met Ser Lys Ser Arg Val Tyr Ala Asp Val Asn Val Leu Arg Pro Arg
  1               5                  10                  15
```

Glu Tyr Trp Asp Tyr Glu Ala Leu Thr Val Gln Trp Gly Asp Gln Asp
                20                  25                  30

Asp Tyr Glu Val Val Arg Lys Ile Gly Arg Gly Lys Tyr Ser Glu Val
            35                  40                  45

Phe Glu Gly Leu Asn Val Asn Ser Asn Glu Arg Cys Val Ile Lys Ile
50                  55                  60

Leu Lys Pro Val Lys Lys Lys Ile Lys Arg Glu Ile Lys Ile Leu
65                  70                  75                  80

Gln Asn Leu Cys Gly Gly Pro Asn Val Ile Lys Leu Leu Asp Ile Val
                85                  90                  95

Arg Asp Gln His Ser Lys Thr Pro Ser Leu Val Phe Glu Phe Val Asn
            100                 105                 110

Ser Thr Asp Phe Lys Val Leu Tyr Pro Thr Leu Ser Asp Tyr Asp Ile
            115                 120                 125

Arg Tyr Tyr Ile Tyr Glu Leu Leu Lys Ala Leu Asp Phe Cys His Ser
130                 135                 140

Gln Gly Ile Met His Arg Asp Val Lys Pro His Asn Val Met Ile Asp
145                 150                 155                 160

His Glu Leu Arg Lys Leu Arg Leu Ile Asp Trp Gly Leu Ala Glu Phe
                165                 170                 175

Tyr His Pro Gly Lys Glu Tyr Asn Val Arg Val Ala Ser Arg Tyr Phe
            180                 185                 190

Lys Gly Pro Glu Leu Leu Val Asp Leu Gln Asp Tyr Asp Tyr Ser Leu
            195                 200                 205

Asp Met Trp Ser Leu Gly Cys Met Phe Ala Gly Met Ile Phe Arg Lys
210                 215                 220

Glu Pro Phe Phe Tyr Gly His Asp Asn His Asp Gln Leu Val Lys Ile
225                 230                 235                 240

Ala Lys Val Leu Gly Thr Asp Glu Leu Asn Ala Tyr Leu Asn Lys Tyr
                245                 250                 255

His Leu Glu Leu Asp Pro Gln Leu Asp Ala Leu Val Gly Arg His Ser
            260                 265                 270

Arg Lys Pro Trp Ser Arg Phe Val Asn Pro Asp Asn Gln His Leu Val
            275                 280                 285

Ser Pro Glu Ala Ile Asp Phe Leu Asp Lys Leu Leu Arg Tyr Asp His
290                 295                 300

Gln Asp Arg Leu Thr Ala Lys Glu Ala Met Ala His Pro Tyr Phe Ser
305                 310                 315                 320

Gln Val Arg Ala Ala Glu Ser Ser Arg Met Arg Thr Gln
                325                 330

<210> SEQ ID NO 7
<211> LENGTH: 345
<212> TYPE: PRT
<213> ORGANISM: Beta vulgaris

<400> SEQUENCE: 7

Met Glu Leu Thr Leu Thr Arg Pro Asp Asp Trp His Leu His Leu Arg
1               5                   10                  15

Asp Gly Asp Leu Leu Ala Ala Val Ala Pro His Ser Ala Arg His Phe
            20                  25                  30

Gly Arg Ala Ile Val Met Pro Asn Leu Arg Pro Pro Val Thr Thr Thr
        35                  40                  45

Gly Ala Ala Ile Ala Tyr Arg Lys Ser Ile Met Glu Val Leu Pro Asp
50                  55                  60

```
Asp Ser Asp Phe Asn Pro Leu Met Thr Leu Tyr Leu Thr Asp Thr Thr
65                  70                  75                  80

Ser Pro Asn Glu Ile Lys Leu Ala Arg Lys Ser Glu Val Val Tyr Ala
                85                  90                  95

Val Lys Leu Tyr Pro Ala Gly Ala Thr Thr Asn Ser Gln Asp Gly Val
            100                 105                 110

Thr Asp Leu Leu Gly Lys Cys Leu Pro Val Leu Glu Glu Met Ala Glu
        115                 120                 125

Gln Asp Met Pro Leu Leu Val His Gly Glu Val Thr Asp Pro Asp Val
    130                 135                 140

Asp Ile Phe Asp Arg Glu Lys Val Phe Ile Glu Ser Val Leu Arg Pro
145                 150                 155                 160

Leu Ile Gln Lys Leu Pro Gln Leu Lys Val Met Glu His Ile Thr
                165                 170                 175

Thr Ala Asp Ala Val Lys Phe Ile Glu Ser Cys Asn Gly Gly Asn Val
            180                 185                 190

Ala Ala Thr Val Thr Pro Gln His Leu Val Leu Asn Arg Asn Ser Leu
        195                 200                 205

Phe Gln Gly Gly Leu Gln Pro His Asn Tyr Cys Leu Pro Val Leu Lys
210                 215                 220

Arg Glu Ile His Arg Gln Ala Leu Val Ser Ala Val Thr Ser Gly Ser
225                 230                 235                 240

Lys Gln Tyr Phe Leu Gly Thr Asp Ser Ala Pro His Glu Arg Arg Arg
                245                 250                 255

Lys Glu Cys Ser Cys Gly Cys Ala Gly Ile Tyr Asn Ser Pro Val Ala
            260                 265                 270

Leu Ser Leu Tyr Ala Lys Val Phe Glu Glu Ala Gly Ala Leu Asp Lys
        275                 280                 285

Leu Glu Ala Phe Thr Ser Phe Asn Gly Pro Asp Phe Tyr Gly Leu Pro
290                 295                 300

Arg Asn Thr Ser Lys Ile Lys Leu Lys Lys Glu Pro Trp Lys Val Leu
305                 310                 315                 320

Glu Arg Ile Pro Phe Pro Ser Gly Glu Ile Pro Met Phe Ala Gly
                325                 330                 335

Gln Met Leu Asp Trp Lys Pro Ser Phe
            340                 345

<210> SEQ ID NO 8
<211> LENGTH: 144
<212> TYPE: PRT
<213> ORGANISM: Beta vulgaris

<400> SEQUENCE: 8

Met Pro Lys Asn Lys Gly Lys Gly Gly Lys Asn Arg Lys Arg Gly Lys
1               5                   10                  15

Asn Glu Ala Asp Asp Glu Lys Arg Glu Leu Val Phe Lys Glu Asp Gly
            20                  25                  30

Gln Glu Tyr Ala Gln Val Val Arg Met Leu Gly Asn Gly Arg Cys Glu
        35                  40                  45

Ala Thr Cys Ile Asp Tyr Val Lys Arg Leu Cys His Ile Arg Gly Lys
    50                  55                  60

Met His Lys Lys Val Trp Ile Ala Ala Gly Asp Ile Ile Leu Val Gly
65                  70                  75                  80

Leu Arg Asp Tyr Gln Asp Asp Lys Ala Asp Val Ile Leu Lys Tyr Met
```

```
                    85                  90                  95
Pro Asp Glu Ala Arg Leu Leu Lys Ala Tyr Gly Glu Leu Pro Asp Asn
                100                 105                 110
Ile Arg Leu Asn Glu Gly Val Ala Asn Leu Asp Glu Glu Asp Asp Gly
            115                 120                 125
Gly Ala Asp Asp Tyr Ile Glu Phe Glu Asp Glu Ile Asp Lys Ile
        130                 135                 140

<210> SEQ ID NO 9
<211> LENGTH: 156
<212> TYPE: PRT
<213> ORGANISM: Beta vulgaris

<400> SEQUENCE: 9

Met Val Arg Lys Arg Phe Gln Asp Val Gln Thr Gly Ile Gln Trp Ala
1               5                   10                  15
Lys Val Leu Arg Lys Val Gly Leu Gly Lys Glu Asp Arg Tyr Phe Trp
                20                  25                  30
Lys Gln Val Gly Lys Ala Leu Leu Cys Thr Tyr Ala Val Phe Gly Ala
            35                  40                  45
Ala Trp Val Tyr Asn Glu Thr Ser Pro Leu Gly Trp Trp Thr Leu Lys
        50                  55                  60
Pro Arg Pro Lys Glu Glu Lys Glu Leu Ala His Leu Tyr Glu Arg Arg
65                  70                  75                  80
Glu Phe Pro Tyr Pro Gly Asp Lys Glu Ala Met Glu Glu Phe Val Thr
                85                  90                  95
Lys Gly Gly Met Ile Gly Thr Thr Ile Gly Pro Lys Gly Thr Val Glu
                100                 105                 110
Thr Asp Lys Asp Ser Phe Asn Tyr Gln Lys Ala Leu Gln Asp Lys Lys
            115                 120                 125
Phe Glu Gln Glu Ala His Lys Leu Trp Phe Arg Met Arg Asn Glu Val
        130                 135                 140
Val Ala Glu Leu Gln Glu Lys Gly Phe Asp Val Glu
145                 150                 155

<210> SEQ ID NO 10
<211> LENGTH: 292
<212> TYPE: PRT
<213> ORGANISM: Beta vulgaris

<400> SEQUENCE: 10

Met Met Gly Glu Gly Asn Arg Asp Lys Ser Lys Lys Lys Lys Lys Lys
1               5                   10                  15
Arg Gly Gly Ala Lys Arg Arg Met Thr Val Glu Gln Thr Ser Ala Leu
                20                  25                  30
Lys Ser Val Asn Glu Trp Val Tyr Leu Ala Gln His Ala Asp Glu Gln
            35                  40                  45
Glu Lys Ile Lys Glu Asp Asp Phe Leu Pro Glu Ile Met Arg Ile Ala
        50                  55                  60
Arg Val Ser Glu Asn Ile Val Phe Glu Leu Ser His Thr Ile Cys
65                  70                  75                  80
Ser Asp Gly Phe Leu Ser Pro Ser Ala Leu Val Glu Lys Ala His Gln
                85                  90                  95
Asn Gly Val Lys Val Leu Ala Leu Thr Asp His Asp Thr Met Ser Gly
                100                 105                 110
Ile Pro Glu Ala Leu Gln Ala Ala Gly Arg Phe Gly Ile Lys Ile Ile
```

-continued

```
                115                 120                 125
Pro Gly Val Glu Ile Ser Ser Val Phe Ser Thr Thr Arg Asp Glu Ser
    130                 135                 140
Glu Ala Glu Glu Pro Val His Ile Leu Ala Tyr Tyr Ser Ser Cys Gly
145                 150                 155                 160
Pro Ala Arg Phe Glu Glu Leu Asp Gln Phe Leu Ala Asn Ile Arg Asp
                165                 170                 175
Gly Arg Tyr Leu Arg Ala Lys Asn Met Leu Ala Lys Leu Ala Lys Leu
            180                 185                 190
Lys Lys Pro Val Lys Trp Glu Arg Val Ile Lys Ile Ala Gly Asn Gly
        195                 200                 205
Val Ala Pro Gly Arg Leu His Val Ala Arg Ala Leu Leu Glu Ala Gly
    210                 215                 220
His Val Glu Asp Leu Lys Gln Ala Phe Asp Arg Tyr Leu His Asp Gly
225                 230                 235                 240
Gly Pro Ala Tyr Ser Lys Gly Ser Glu Pro Ser Ala Glu Glu Ala Val
                245                 250                 255
Gln Met Val Cys Lys Thr Gly Gly Ile Ala Val Leu Ala His Pro Trp
            260                 265                 270
Ala Leu Lys Asn Pro Ser Pro Val Val Asn Arg Leu Lys Gly Gly Arg
        275                 280                 285
Ser Ser Trp Asn
    290

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
atggattaga attctcatag agttgtaagg tctcag                              36

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
cctcagttct cgagtttata aatggaaatc agtggtgg                            38

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
cgaagctctc actgttcaat gg                                             22

<210> SEQ ID NO 14
<211> LENGTH: 23
<212> TYPE: DNA
<213> ORGANISM: Artificial Sequence
<220> FEATURE:
<223> OTHER INFORMATION: primer
```

-continued

```
<400> SEQUENCE: 14
ggatgtgcca ttgcttctt tgc                                              23

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ctctcaagtt agagctgcag a                                               21

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
gctattagca aactatatta agtg                                            24

<210> SEQ ID NO 17
<211> LENGTH: 333
<212> TYPE: PRT
<213> ORGANISM: Arabidopsis thaliana

<400> SEQUENCE: 17
```

Met Ser Lys Ala Arg Val Tyr Thr Asp Val Asn Val Ile Arg Pro Lys
1               5                   10                  15

Asp Tyr Trp Asp Tyr Glu Ser Leu Asn Val Gln Trp Gly Glu Gln Asp
            20                  25                  30

Asp Tyr Glu Val Val Arg Lys Val Gly Arg Gly Lys Tyr Ser Glu Val
        35                  40                  45

Phe Glu Gly Ile Asn Met Asn Asn Asn Glu Lys Cys Ile Ile Lys Ile
    50                  55                  60

Leu Lys Pro Val Lys Lys Lys Glu Ile Arg Arg Glu Ile Lys Ile Leu
65                  70                  75                  80

Gln Asn Leu Cys Gly Gly Pro Asn Ile Val Lys Leu Leu Asp Val Val
                85                  90                  95

Arg Asp Gln His Ser Lys Thr Pro Ser Leu Ile Phe Glu Tyr Val Asn
            100                 105                 110

Ser Thr Asp Phe Lys Val Leu Tyr Pro Thr Leu Thr Asp Tyr Asp Ile
        115                 120                 125

Arg Tyr Tyr Ile Tyr Glu Leu Leu Lys Ala Leu Asp Phe Cys His Ser
    130                 135                 140

Gln Gly Ile Met His Arg Asp Val Lys Pro His Asn Val Met Ile Asp
145                 150                 155                 160

His Gly Leu Arg Lys Leu Arg Leu Ile Asp Trp Gly Leu Ala Glu Phe
                165                 170                 175

Tyr His Pro Gly Lys Glu Tyr Asn Val Arg Val Ala Ser Arg Tyr Phe
            180                 185                 190

Lys Gly Pro Glu Leu Leu Val Asp Leu Gln Asp Tyr Asp Tyr Ser Leu
        195                 200                 205

Asp Met Trp Ser Leu Gly Cys Met Phe Ala Gly Met Ile Phe Arg Lys
    210                 215                 220

Glu Pro Phe Phe Tyr Gly His Asp Asn Gln Asp Gln Leu Val Lys Ile

```
                225                 230                 235                 240
        Ala Lys Val Leu Gly Thr Asp Glu Leu Asn Ala Tyr Leu Asn Lys Tyr
                        245                 250                 255

Gln Leu Glu Leu Asp Thr Gln Leu Glu Ala Leu Val Gly Arg His Ser
                        260                 265                 270

Arg Lys Pro Trp Ser Lys Phe Ile Asn Ala Asp Asn Arg His Leu Val
                        275                 280                 285

Ser Pro Glu Ala Ile Asp Tyr Leu Asp Lys Leu Leu Arg Tyr Asp His
                        290                 295                 300

Gln Asp Arg Leu Thr Ala Lys Glu Ala Met Ala His Pro Tyr Phe Ala
        305                 310                 315                 320

Gln Val Arg Ala Ala Glu Ser Ser Arg Met Arg Thr Gln
                        325                 330

<210> SEQ ID NO 18
<211> LENGTH: 332
<212> TYPE: PRT
<213> ORGANISM: Zea mays

<400> SEQUENCE: 18

Met Ser Lys Ala Arg Val Tyr Ala Asp Val Asn Val Leu Arg Pro Lys
1               5                   10                  15

Glu Tyr Trp Asp Tyr Glu Ala Leu Thr Val Gln Trp Gly Glu Gln Asp
                20                  25                  30

Asp Tyr Glu Val Val Arg Lys Val Gly Arg Gly Lys Tyr Ser Glu Val
            35                  40                  45

Phe Glu Gly Ile Asn Val Asn Asn Asn Glu Lys Cys Ile Ile Lys Ile
        50                  55                  60

Leu Lys Pro Val Lys Lys Lys Lys Ile Lys Arg Glu Ile Lys Ile Leu
65                  70                  75                  80

Gln Asn Leu Cys Gly Gly Pro Asn Ile Val Lys Leu Leu Asp Ile Val
                85                  90                  95

Arg Asp Gln His Ser Lys Thr Pro Ser Leu Ile Phe Glu Tyr Val Asn
            100                 105                 110

Asn Thr Asp Phe Lys Val Leu Tyr Pro Thr Leu Thr Asp Tyr Asp Ile
        115                 120                 125

Arg Tyr Tyr Ile Tyr Glu Leu Leu Lys Ala Leu Asp Tyr Cys His Ser
    130                 135                 140

Gln Gly Ile Met His Arg Asp Val Lys Pro His Asn Val Met Ile Asp
145                 150                 155                 160

His Glu Leu Arg Lys Leu Arg Leu Ile Asp Trp Gly Leu Ala Glu Phe
                165                 170                 175

Tyr His Pro Gly Lys Glu Tyr Asn Val Arg Val Ala Ser Arg Tyr Phe
            180                 185                 190

Lys Gly Pro Glu Leu Leu Val Asp Leu Gln Asp Tyr Asp Tyr Ser Leu
        195                 200                 205

Asp Met Trp Ser Leu Gly Cys Met Phe Ala Gly Met Ile Phe Arg Lys
    210                 215                 220

Glu Pro Phe Phe Tyr Gly His Asp Asn His Asp Gln Leu Val Lys Ile
225                 230                 235                 240

Ala Lys Val Leu Gly Thr Asp Gly Leu Asn Val Tyr Leu Asn Lys Tyr
                245                 250                 255

Arg Ile Glu Leu Asp Pro Gln Leu Glu Ala Leu Val Gly Arg His Ser
            260                 265                 270
```

```
Arg Lys Pro Trp Leu Lys Phe Met Asn Ala Asp Asn Gln His Leu Val
        275                 280                 285

Ser Pro Glu Ala Ile Asp Phe Leu Asp Lys Leu Leu Arg Tyr Asp His
    290                 295                 300

Gln Glu Arg Leu Thr Ala Leu Glu Ala Met Thr His Pro Tyr Phe Gln
305                 310                 315                 320

Gln Val Arg Ala Ala Glu Asn Ser Arg Thr Arg Ala
                325                 330
```

<210> SEQ ID NO 19
<211> LENGTH: 391
<212> TYPE: PRT
<213> ORGANISM: Rattus norvegicus

<400> SEQUENCE: 19

```
Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
290                 295                 300

Leu Arg Tyr Asp His Gln Ser Arg Leu Thr Ala Arg Glu Ala Met Glu
305                 310                 315                 320
```

```
His Pro Tyr Phe Tyr Thr Val Val Lys Asp Gln Ala Arg Met Ser Ser
                325                 330                 335

Ala Gly Met Ala Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Asn Ser Leu Gly Ile Pro Val Pro
    370                 375                 380

Ala Ala Ala Gly Ala Gln Gln
385                 390

<210> SEQ ID NO 20
<211> LENGTH: 350
<212> TYPE: PRT
<213> ORGANISM: Xenopus laevis

<400> SEQUENCE: 20

Met Ser Gly Pro Val Pro Ser Arg Ala Arg Val Tyr Thr Asp Val Asn
1               5                   10                  15

Thr His Arg Pro Arg Asp Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
```

```
                290                 295                 300
Leu Arg Tyr Asp His Gln Thr Arg Leu Thr Ala Arg Glu Ala Met Asp
305                 310                 315                 320

His Pro Tyr Phe Tyr Pro Ile Val Lys Asp Gln Ser Arg Met Ala Ala
                325                 330                 335

Leu Ile Cys Pro Val Ala Ala His Pro Ser Val Ala Pro Val
                340                 345                 350

<210> SEQ ID NO 21
<211> LENGTH: 339
<212> TYPE: PRT
<213> ORGANISM: Saccharomyces cerevisiae

<400> SEQUENCE: 21

Met Pro Leu Pro Pro Ser Thr Leu Asn Gln Lys Ser Asn Arg Val Tyr
1               5                   10                  15

Ser Val Ala Arg Val Tyr Lys Asn Ala Cys Glu Glu Arg Pro Gln Glu
                20                  25                  30

Tyr Trp Asp Tyr Glu Gln Gly Val Thr Ile Asp Trp Gly Lys Ile Ser
            35                  40                  45

Asn Tyr Glu Ile Ile Asn Lys Ile Gly Arg Gly Lys Tyr Ser Glu Val
        50                  55                  60

Phe Ser Gly Arg Cys Ile Val Asn Asn Gln Lys Cys Val Ile Lys Val
65                  70                  75                  80

Leu Lys Pro Val Lys Met Lys Lys Ile Tyr Arg Glu Leu Lys Ile Leu
                85                  90                  95

Thr Asn Leu Thr Gly Gly Pro Asn Val Val Gly Leu Tyr Asp Ile Val
                100                 105                 110

Gln Asp Ala Asp Ser Lys Ile Pro Ala Leu Ile Phe Glu Glu Ile Lys
            115                 120                 125

Asn Val Asp Phe Arg Thr Leu Tyr Pro Thr Phe Lys Leu Pro Asp Ile
        130                 135                 140

Gln Tyr Tyr Phe Thr Gln Leu Leu Ile Ala Leu Asp Tyr Cys His Ser
145                 150                 155                 160

Met Gly Ile Met His Arg Asp Val Lys Pro Gln Asn Val Met Ile Asp
                165                 170                 175

Pro Thr Glu Arg Lys Leu Arg Leu Ile Asp Trp Gly Leu Ala Glu Phe
                180                 185                 190

Tyr His Pro Gly Val Asp Tyr Asn Val Arg Val Ala Ser Arg Tyr His
            195                 200                 205

Lys Gly Pro Glu Leu Leu Val Asn Leu Asn Gln Tyr Asp Tyr Ser Leu
        210                 215                 220

Asp Leu Trp Ser Val Gly Cys Met Leu Ala Ala Ile Val Phe Lys Lys
225                 230                 235                 240

Glu Pro Phe Phe Lys Gly Ser Ser Asn Pro Asp Gln Leu Val Lys Ile
                245                 250                 255

Ala Thr Val Leu Gly Thr Lys Glu Leu Leu Gly Tyr Leu Gly Lys Tyr
                260                 265                 270

Gly Leu His Leu Pro Ser Glu Tyr Asp Asn Ile Met Arg Asp Phe Thr
            275                 280                 285

Lys Lys Ser Trp Thr His Phe Ile Thr Ser Glu Thr Lys Leu Ala Val
        290                 295                 300

Pro Glu Val Val Asp Leu Ile Asp Asn Leu Leu Arg Tyr Asp His Gln
305                 310                 315                 320
```

Glu Arg Leu Thr Ala Lys Glu Ala Met Asp His Lys Phe Phe Lys Thr
            325                 330                 335

Lys Phe Glu

<210> SEQ ID NO 22
<211> LENGTH: 12
<212> TYPE: PRT
<213> ORGANISM: Artificial Sequence
<220> FEATURE:
<223> OTHER INFORMATION: Tag 100 epitope

<400> SEQUENCE: 22

Glu Glu Thr Ala Arg Phe Gln Pro Gly Tyr Arg Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: c-myc epitope

<400> SEQUENCE: 23

Glu Gln Lys Leu Ile Ser Glu Glu Asp Leu
1               5                   10

<210> SEQ ID NO 24
<211> LENGTH: 7
<212> TYPE: PRT
<213> ORGANISM: Artificial Sequence
<220> FEATURE:
<223> OTHER INFORMATION: FLAG-epitope

<400> SEQUENCE: 24

Asp Tyr Lys Asp Asp Asp Lys
1               5

<210> SEQ ID NO 25
<211> LENGTH: 9
<212> TYPE: PRT
<213> ORGANISM: Artificial Sequence
<220> FEATURE:
<223> OTHER INFORMATION: HA epitope

<400> SEQUENCE: 25

Tyr Pro Tyr Asp Val Pro Asp Tyr Ala
1               5

<210> SEQ ID NO 26
<211> LENGTH: 12
<212> TYPE: PRT
<213> ORGANISM: Artificial Sequence
<220> FEATURE:
<223> OTHER INFORMATION: protein C epitope

<400> SEQUENCE: 26

Glu Asp Gln Val Asp Pro Arg Leu Ile Asp Gly Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: VSV epitope

<400> SEQUENCE: 27

```
-continued

Tyr Thr Asp Ile Glu Met Asn Arg Leu Gly Lys
1               5                   10

<210> SEQ ID NO 28
<211> LENGTH: 7
<212> TYPE: PRT
<213> ORGANISM: Artificial Sequence
<220> FEATURE:
<223> OTHER INFORMATION: highly basic domain

<400> SEQUENCE: 28

Lys Lys Lys Lys Ile Lys Arg
1               5
```